United States Patent
Hopman et al.

(10) Patent No.: US 10,182,934 B2
(45) Date of Patent: Jan. 22, 2019

(54) REVERSIBLY ENGAGED FORCE-CONTROLLED BUCKLE AND PELVIC RING SUPPORT DEVICE INCORPORATING SUCH A BUCKLE

(71) Applicant: The Seaberg Company, Inc., Wilsonville, OR (US)

(72) Inventors: Lance David Hopman, Tigard, OR (US); Lane Michael Johnson, Chandler, AZ (US); Eric E. Batdorf, Oregon City, OR (US); Brian Lux, Cornelius, OR (US); Nolan Brophy, San Jose, CA (US); Aaron Lundquist, Petaluma, CA (US); Matthew Malone, Burien, WA (US); Kenneth J. Courian, Portland, OR (US)

(73) Assignee: The Seaberg Company, Inc., Wilsonville, OR (US)

( * ) Notice: Subject to any disclaimer, the term of this patent is extended or adjusted under 35 U.S.C. 154(b) by 808 days.

(21) Appl. No.: 14/097,018

(22) Filed: Dec. 4, 2013

(65) Prior Publication Data
US 2014/0155797 A1 Jun. 5, 2014

Related U.S. Application Data

(60) Provisional application No. 61/733,058, filed on Dec. 4, 2012.

(51) Int. Cl.
*A44B 11/24* (2006.01)
*A61F 5/01* (2006.01)

(52) U.S. Cl.
CPC .......... *A61F 5/0102* (2013.01); *A61F 5/0193* (2013.01); *Y10T 24/407* (2015.01)

(58) Field of Classification Search
CPC .......... A61F 5/0193; A61F 5/02; A61F 5/028; A61F 5/03; A44B 11/2553;
(Continued)

(56) References Cited

U.S. PATENT DOCUMENTS

| 4,715,364 A | 12/1987 | Noguchi |
| 4,991,573 A | 2/1991 | Miller |

(Continued)

FOREIGN PATENT DOCUMENTS

| WO | 2011016824 | 2/2011 |

OTHER PUBLICATIONS

WIPO, International Search Report, dated Apr. 21, 2014, issued in pending international application PCT/US13/073191 (WO2014/089243).

(Continued)

*Primary Examiner* — Kari Rodriquez
(74) *Attorney, Agent, or Firm* — Chernoff, Vilhauer, McClung & Stenzel, LLP

(57) ABSTRACT

A belt-like hip-girdling pelvic sling device for maintaining a desired amount of tension surrounding a person's hips and pelvis to securely support and stabilize a fractured pelvis, including a force-controlled buckle that automatically latches to control the tension and that includes a releasable latching mechanism. The latching mechanism maintains engagement of the buckle with a strap at the required position of the strap with respect to the buckle. The latching mechanism includes a movable member of the buckle that is moved to and latched in a position in which the buckle engages the strap, once a desired amount of tension is reached, limiting and maintaining the required tension.

22 Claims, 24 Drawing Sheets

(58) Field of Classification Search
CPC ............ A44B 11/2584; A44B 11/2588; A44B 11/2592; A44B 11/22; A44B 11/2526; A44B 11/006; A44B 11/10; A44B 11/20; A44B 11/226; A44B 11/24
See application file for complete search history.

(56) References Cited

U.S. PATENT DOCUMENTS

| | | | |
|---|---|---|---|
| 5,086,759 | A | 2/1992 | Buddingh |
| 5,500,959 | A | 3/1996 | Yewer, Jr. |
| 5,830,168 | A | 11/1998 | Finnell et al. |
| 6,066,109 | A | 5/2000 | Buser et al. |
| 6,165,147 | A | 12/2000 | Morrow |
| 6,240,923 | B1 | 6/2001 | Barrick |
| 8,926,536 | B2 | 1/2015 | Hopman et al. |
| 9,028,435 | B2 | 5/2015 | Hopman et al. |
| 2001/0053884 | A1 | 12/2001 | Krieg et al. |
| 2004/0039321 | A1 | 2/2004 | Krieg et al. |
| 2007/0022577 | A1 | 2/2007 | Funo |
| 2007/0130735 | A1* | 6/2007 | Diamond ............... A44B 11/24 24/636 |
| 2009/0300888 | A1 | 12/2009 | Shiue |
| 2010/0071173 | A1* | 3/2010 | Hortnagl ............ A44B 11/2592 24/651 |
| 2011/0034845 | A1* | 2/2011 | Polliack ................ A61F 5/0193 602/19 |
| 2012/0245500 | A1 | 9/2012 | Polliack et al. |
| 2013/0110019 | A1 | 5/2013 | Hopman |
| 2013/0324898 | A1 | 12/2013 | Polliack et al. |

OTHER PUBLICATIONS

WIPO, Written Opinion of the International Searching Authority, dated Apr. 21, 2014, issued in pending international application PCT/US13/073191 (WO2014/089243).

Pyng Medical, "T-Pod Pelvic Stabilization Device" Instruction Sheet, PM-032b, prior to May 2012, Richmond, British Columbia, Canada, 1 page.

European Patent Office, "Extended European Search Report" for EP App. No. 15746775.4, dated Sep. 21, 2017, Munich, Germany, 9 pages.

Korean Intellectual Property Office, "International Search Report and Written Opinion", for PCT App. No. PCT/US2010/001682, dated Mar. 15, 2011, Daejeon, Republic of Korea, 11 pages.

US Patent and Trademark Office, "International Search Report and Written Opinion", for PCT App. No. PCT/US2012/050437, dated Dec. 31, 2012, Alexandria, Virginia, 17 pages.

European Patent Office, "Extended European Search Report" for EP App. No. 10806730.7, dated Jan. 10, 2013, Munich, Germany, 5 pages.

US Patent and Trademark Office, "International Search Report and Written Opinion", for PCT App. No. PCT/US2014/016305, dated May 30, 2014, Alexandria, Virginia, 17 pages.

The International Bureau of WIPO, "Preliminary Report on Patentability" for PCT App. No. PCT/US2010/001682, dated Feb. 7, 2012, Geneva, Switzerland, 5 pages.

The International Bureau of WIPO, "Preliminary Report on Patentability" for PCT App. No. PCT/US2012/050437, dated Feb. 27, 2014, Geneva, Switzerland, 13 pages.

The International Bureau of WIPO, "Preliminary Report on Patentability" for PCT App. No. PCT/US2014/016305, dated Jun. 25, 2015, Geneva, Switzerland, 9 pages.

* cited by examiner

REVERSIBLY ENGAGED FORCE-CONTROLLED BUCKLE AND PELVIC RING SUPPORT DEVICE INCORPORATING SUCH A BUCKLE

CROSS-REFERENCE TO RELATED APPLICATIONS

This application claims the benefit of U.S. Provisional Patent Application Ser. No. 61/733,058 filed Dec. 4, 2012.

BACKGROUND OF THE INVENTION

The present invention relates to medical emergency equipment, and in particular to a buckle for use in a device for supporting and controlling movement of a patient's injured pelvis.

U.S. Pat. Nos. 6,554,784, 7,008,389, and 8,192,383 disclose belt-like hip-girdling pelvis-stabilizing devices each including a buckle and a strap engaged through the buckle so as to place the belt into tension while it encircles a patient's pelvis. The buckle is arranged to engage the strap when a certain tension has been developed in the portion of the device encircling the patient, to prevent excessive tension in the portion of the device encircling the patient. So long as enough tension is retained in an outer part of the strap, extending beyond the buckle, engagement of the buckle with the strap maintains tension in the belt-like device the while the medical provider applying the device secures the outer part of the strap to the main body of the device.

In some versions of such a pelvis-stabilizing device the buckle produces an audible click when the correct amount of tension has been achieved, indicating that one or more prongs are exposed within the buckle and have entered into corresponding holes in the strap. If the outer end of the strap in such a buckle is not properly secured to maintain the amount of tension, however, a part of the buckle may move to hide the prongs, retracting them from engagement with the strap and allowing tension in the hip-girdling device to be reduced.

It is desired, then, to provide a pelvis-stabilizing device including a buckle mechanism that can be used to engage a strap to resist or prevent application of excessive tension, yet to maintain a desired amount of tension in the portion of the device encircling a patient and to facilitate keeping the buckle engaged with the strap while applying the device to a patient, so that tension is retained in the part of the device surrounding the patient while the outer end of the strap is being secured to a main body portion of the device.

SUMMARY OF THE INVENTION

The present invention provides a pelvis stabilizing device including a force-controlled buckle which engages a strap once sufficient tension has been achieved in the strap and thus maintains a required tension in the portion of the device encircling a patient's pelvis. The buckle can maintain tension in the portion of the device encircling a patient even if tension is not continuously maintained in the outer portion of the strap, that is, the portion of the strap extending away from the buckle and which has had to be pulled through the buckle to place into tension the portion of the device encircling the patient.

In one embodiment of the device the force-controlled buckle consists of at least two components, a frame and a slider. In such a device the slider is mounted movably within an opening defined by the frame. In one embodiment of the buckle the slider's motion is resisted by a pair of springs that ordinarily keep the slider in a position obscuring the outer ends of a pair of pins or prongs and thus allow a strap to slide along the slider within the opening defined by the frame while tension is being developed in the strap.

Once a predetermined tension has been developed in the strap the slider is moved by the tension in the strap to a position with respect to the frame exposing the tips of the pins or prongs, and the pins or prongs are extended into corresponding holes provided in the strap and prevent the strap from being placed into greater tension. Upon movement of the slider to a particular position relative to the frame, a latch mechanism engages portions of the slider and the frame with one another and prevents the slider from moving with respect to the frame and again obscuring the prongs, even if tension in the strap is relieved so that the strap no longer holds the slider in its moved position with respect to the frame.

The latch mechanism is readily released to disengage the slider from the frame, so that the slider can move to its original position in which it obscures the prongs and allows a strap to slide through the buckle.

In one embodiment, catches are carried on fingers provided on the slider and the fingers are urged by elastic force developed in the fingers to carry the catches into engagement with corresponding receptacles formed in the buckle frame.

In another embodiment, catches can be provided in the frame and arranged to move into engagement with suitable receptacles in the slider.

In another embodiment of the buckle respective holes may be provided in the frame and in the slider in respective locations where the holes would be aligned with each other when tension in the strap had reached the required amount to move the slider with respect to the frame far enough to expose the prongs, and a spring-loaded retaining pin can then move into the holes or through the hole and retain the slider in the required position with respect to the frame.

In yet another embodiment of the buckle, one or more spring-biased levers is carried on the frame and can be moved about a pivot to carry a catch into locking engagement with the slider by an associated spring once the slider has moved. The lever can be manually moved to disengage the catch.

The foregoing and other features of the invention will be more readily understood upon consideration of the following detailed description of the invention taken in conjunction with the accompanying drawings.

BRIEF DESCRIPTION OF THE DRAWINGS

FIG. 4A is a detail view showing a part of the slider and the attached latch-carrying finger of the buckle shown in FIG. 4.

FIG. 10A is a detail view of a portion of the slider and a catch-carrying finger of the buckle shown in FIG. 10.

FIG. 14A is a detail view showing a portion of the slider and the latch-carrying finger that is a part of the buckle shown in FIG. 14.

DETAILED DESCRIPTION OF PREFERRED EMBODIMENTS

Figure 1:
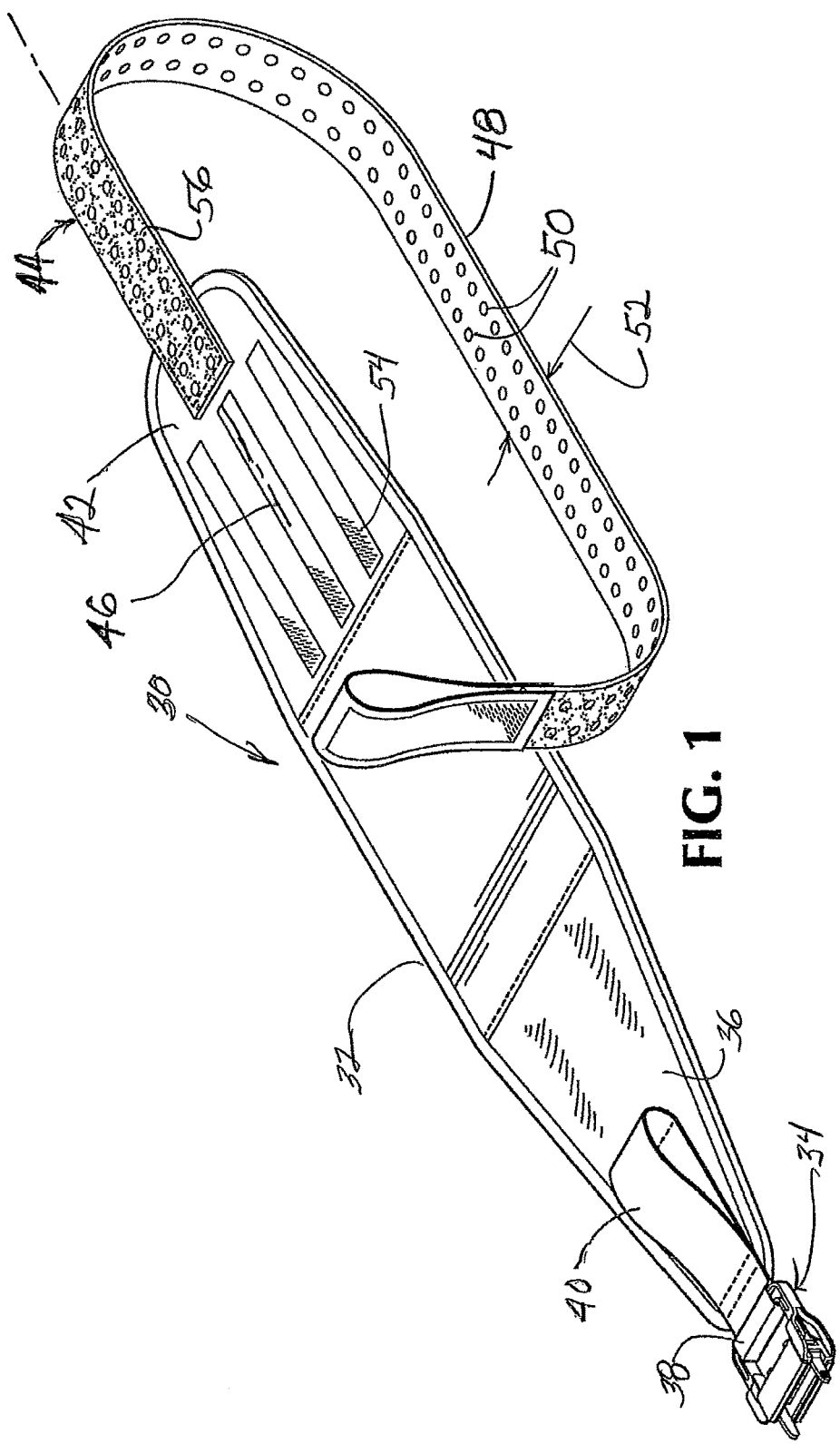
FIG. 1 is an isometric view of a pelvis-stabilizing device including a tension-retaining force-controlled buckle that is an exemplary embodiment of an aspect of the present invention.
Figure 2:
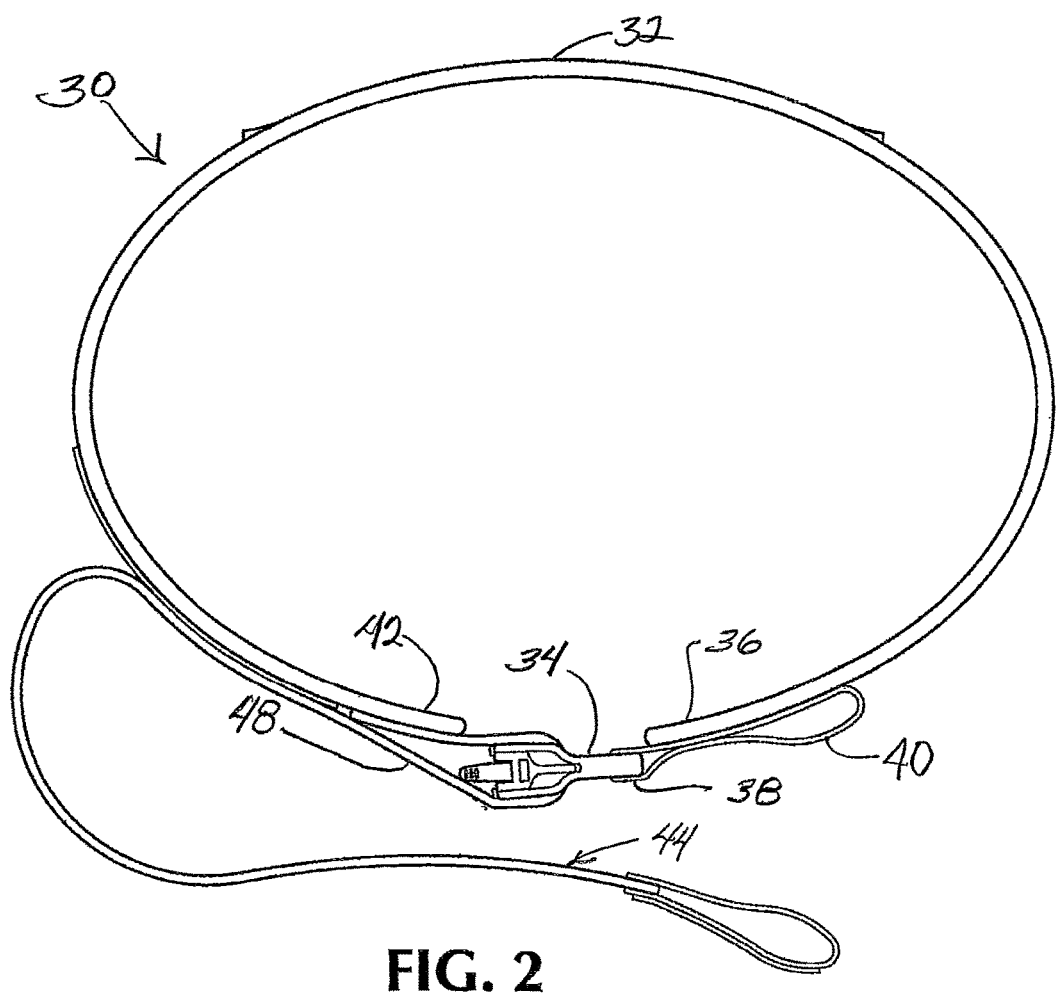
FIG. 2 is a top plan view showing the pelvis-stabilizing device shown in FIG. 1 in tension and with the strap shown secured so as to maintain tension and keep the buckle engaged with the strap while the device is in place encircling a person's pelvis.

Referring now to the drawings which form a part of the disclosure herein, in FIG. 1 a pelvis supporting and stabilizing device 30 for stabilizing a fractured pelvis, often called a pelvic sling, is shown in a condition in which it is ready for application to a person to provide stabilization and support for a fractured pelvic ring. The device 30 is used by placing it on the person so that it encircles the hip region of the person, as shown in FIG. 2. A main body portion 32 is of strong flexible material and has the general shape of a wide belt. A buckle 34 is attached to a first end portion 36 of the main body portion by a small loop 38 of a strap of strong fabric such as woven Nylon webbing that is permanently attached to the first end portion 36, as by being sewn in securely to it. As used herein, the term "permanently attached" means that removal and reattachment are not easily accomplished by a user and cannot be accomplished readily without the use of equipment similar to that needed for initial manufacture of the pelvic sling 30. A large loop 40 of fabric which may be similar to that of the small loop 36 may also be attached to the first end portion 36 of the main body so that the large loop 40 can be used as a handle by a person applying the pelvic sling 30 to an injured person, as will be explained more fully presently.

At a second end portion 42 of the main body portion 32, opposite the first end portion 36, an inner end of an elongate flexible strap 44 is permanently attached to the main body portion 32, as by being sewn, riveted, or thermally or sonically welded securely to the second end portion 42. The strap 44 may be made of strong fabric such as Nylon webbing and extends longitudinally away from the second end portion 42, generally aligned with a longitudinal axis 46 of the main body portion. An outer end portion of the strap 44 may include a loop of strong fabric such as nylon webbing attached to an intermediate portion 48 of the strap, so that the loop is available for use as a handle to pull the strap away from the buckle, in applying the pelvic sling 30 to a patient.

Pairs of holes 50 may be defined in the intermediate portion of the strap 44. The holes 50 of each pair are aligned with each other transversely across the width 52 of the strap, which may be about 2 inches, for example. Adjacent pairs of holes 50 may be spaced apart evenly longitudinally of the strap at a pitch of, for example, about 0.625 inch, so as to permit the effective circumference of the pelvic sling to be adjusted in increments small enough to provide a desirable amount of tension in the pelvic sling 30 as it encircles a person's hips to stabilize a fractured pelvis.

Figure 3:
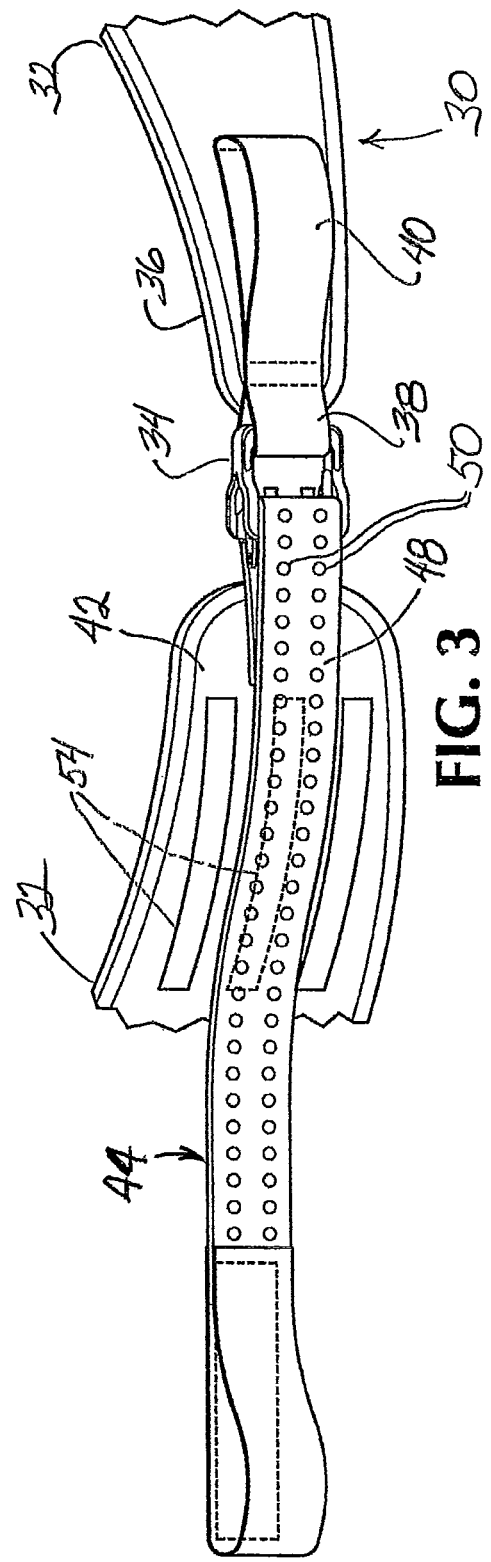
FIG. 3 is an isometric front view of the first and second end portions of the main body of the pelvis-stabilizing device shown in FIGS. 1 and 2, illustrating the device secured and under tension around a person.

An area 54 of a hook-bearing fastener material, such as that well known under the trademark Velcro®, capable of matingly engaging a corresponding loop-bearing flexible fastener material, may be provided on the second end portion 42 of the main body, and an exterior side of the intermediate portion 48 of the strap may be covered by a layer 56 of a flexible loop-bearing fastener material, securely attached to the strap 44, as by being sewn to the webbing. Such loop-bearing fastener material ideally may be present along the entire exterior side or face of the strap 44, the side that is exposed so as to face toward the exterior of the second end portion 42 of the main body portion 32, and may be present on the inner end of the strap 44, as shown in FIGS. 1 and 3. Thus, when the strap 44 extends through the buckle 34 and is closely alongside the second end portion 42 of the main body portion 32 as shown in FIGS. 2 and 3, the hook-and-loop fastener material will secure the strap 44 to the second end portion 42.

When the pelvic sling 30 is properly in place on an injured person, it encircles the person's hips and buttocks, and the first and second end portions 36 and 42 face toward each other, with the strap 44 extending through the buckle 34 and doubled back alongside the second end portion 42 on the exterior of the pelvic sling 30.

When the pelvic sling 30 is properly in place, there is a prescribed amount of tension maintained in the main body portion 32 as it encircles the injured person, so that a fracture in the pelvic ring of the person is reduced. This tension is maintained by engagement of the buckle 34 with the strap 44, as shown in FIGS. 2 and 3, where it may be seen that with the desired amount of tension exerted on the buckle 34 by the strap 44, a pair of strap engagement members in the forms of pins 58 extend into the holes 50 in the strap 44, preventing the strap 44 from moving with respect to the buckle 34.

Once the pins 58 engage with the holes 50, the loop-bearing fastener material 56 on the exterior side of the strap 44 is aligned and mated with hook-bearing fastener material 54 on the exterior side of the second end portion 42 of the main body 32, thus keeping the strap 44 from being disengaged from the buckle 34.

As shown in FIGS. 4-9, the buckle 34 is a force-controlled buckle and consists of at least two components, a substantially rigid frame 60 and a sliding block or slider 62 which is mounted in the frame 60 and movable with respect to it. Both the frame 60 and the slider may be molded of suitably strong synthetic plastics resins. With the buckle 34 configured as shown in FIG. 1-4, the rigid frame 60 includes a transversely extending bow portion 64 which can be engaged by the small loop 68 of strap material attached to the first end portion 36 of the main body portion 32 of the pelvic sling 30. The sliding block or slider 62 is movable relative to the buckle frame 60 in a longitudinal direction as indicated by the arrow 66. The frame 60 defines an opening 68 which is a passageway wide enough to receive the strap 44, which extends through the opening 68 when the pelvic sling 30 is in use. When there is little tension involved the strap 44 can slide easily along the convexly curved surface of the contact face 70 of the slider 62 as the strap 44 is pulled to tighten the pelvic sling 30 about a person's pelvis.

A pair of holes 72 is defined in the slider 62, and the pins 58 mentioned above with respect to FIGS. 2 and 3 are aligned with the holes 72 and may extend at least a small distance into the holes. The frame 60 includes a base portion 74, opposite the bow 64, from which the pins 58 extend toward the slider 62 as may be seen best in FIGS. 5-8.

A pair of helical springs 76 extends from the base portion to the interior of the slider. Each of the springs may surround a respective one of the pins 58 between the base 74 and the slider 62. Suitable seats may be provided on the base 74 and the interior of the slider 62 to locate and align the springs. The springs 76 are compressed sufficiently to provide enough force to keep the slider 62 in the position shown in FIGS. 6 and 8 until a desired amount of tension is created in the pelvic sling 30 by pulling the strap 44 through the opening 68 of the buckle 34.

Figures 7, 8:
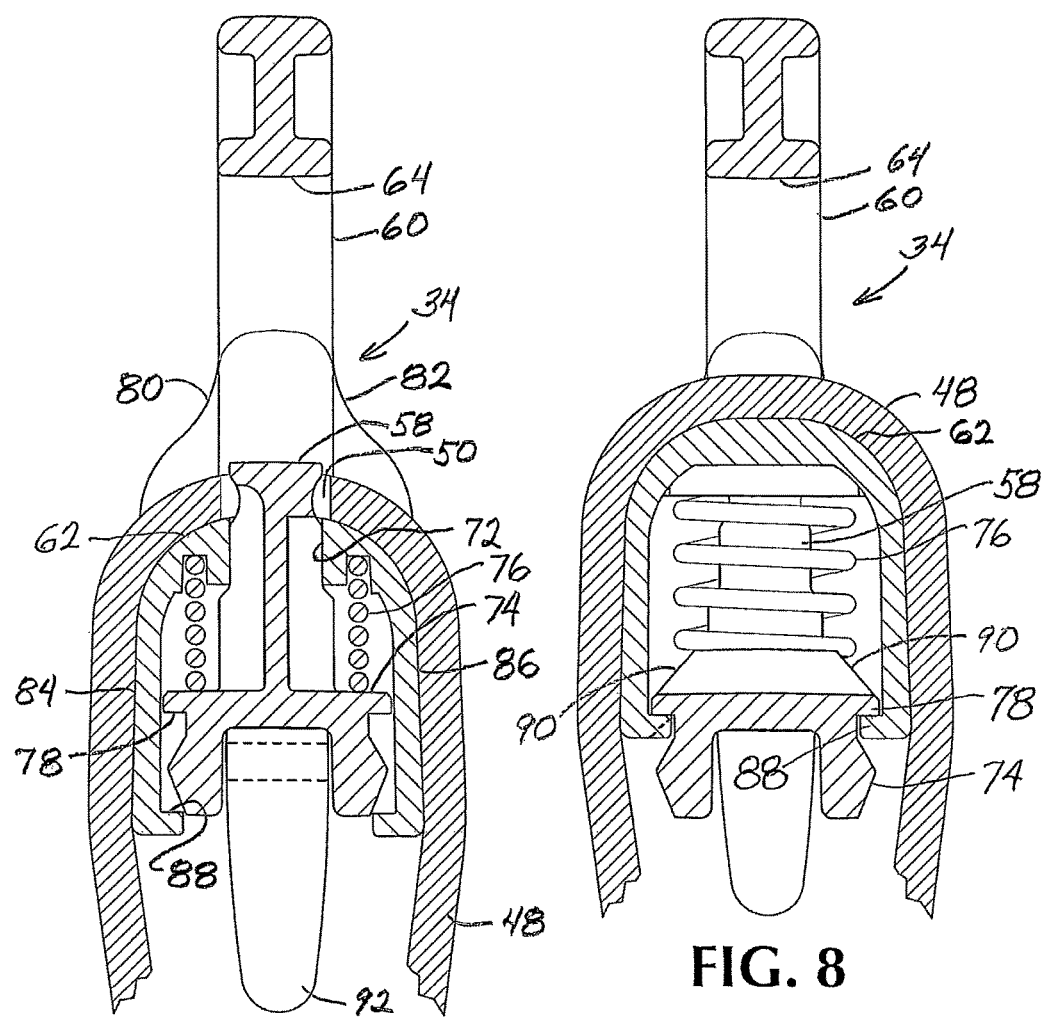
FIG. 7 is a sectional view of the buckle shown in FIG. 4, taken along line 7-7 of FIG. 4, with the buckle in the state in which it is shown in FIG. 4.
FIG. 8 is a sectional view taken along line 8-8 of FIG. 4, showing the buckle in the state in which it is shown in FIG. 6.
Figure 9:
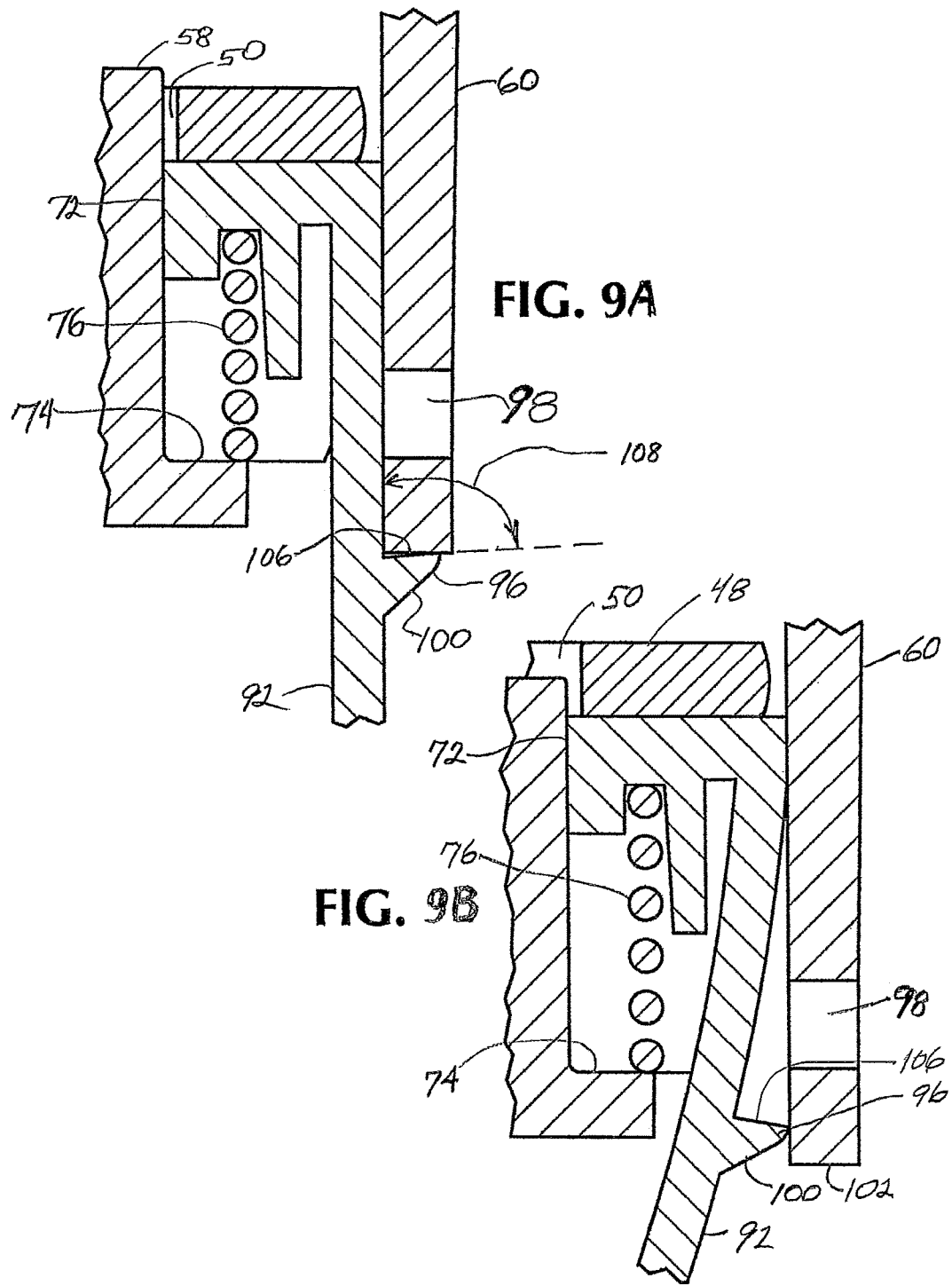
FIG. 9A is a sectional view of a detail of the buckle as shown in FIG. 5, at an enlarged scale.
FIG. 9B is a view similar to FIG. 9A, showing the buckle with its latch between the engaged and disengaged positions.
Figure 10:
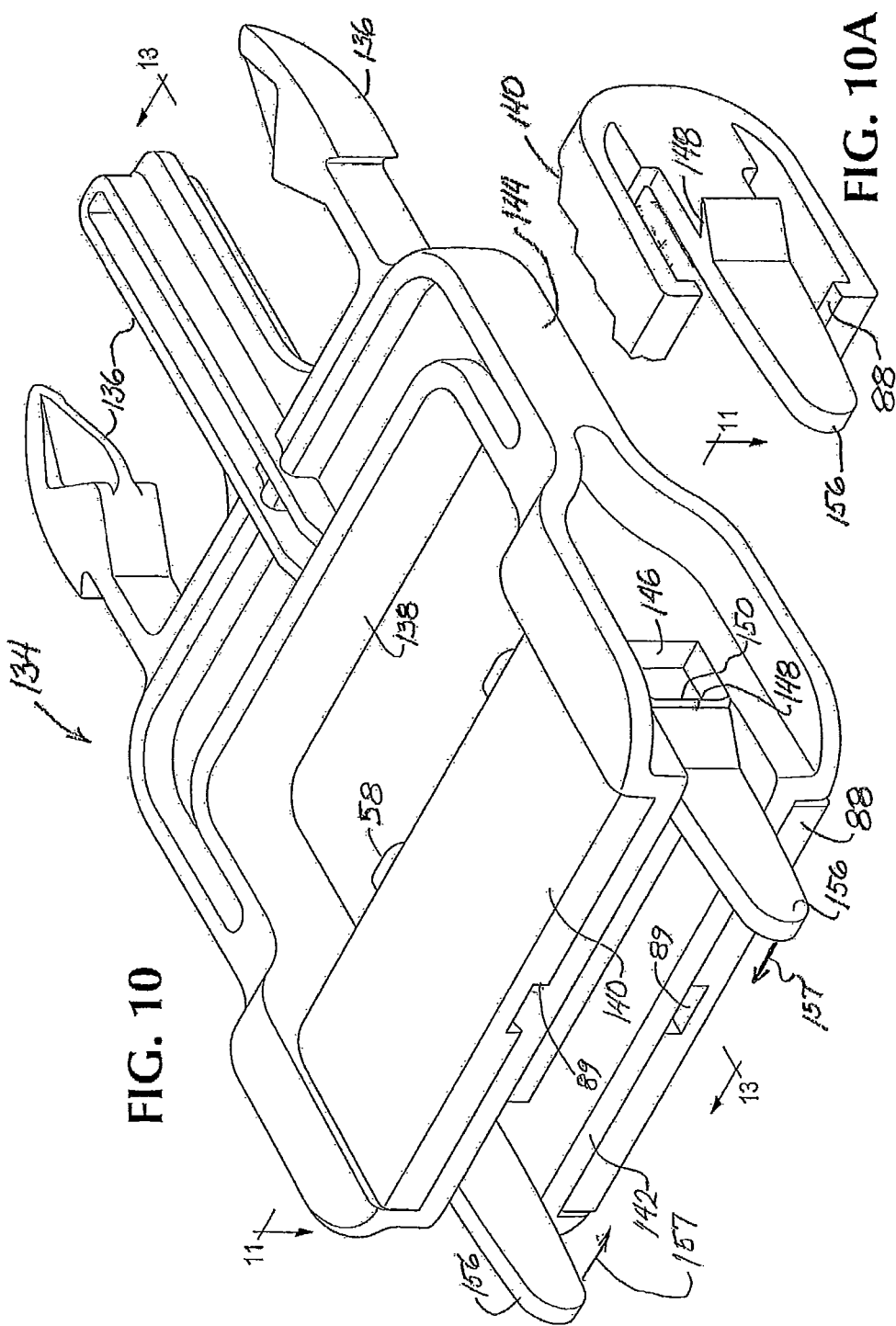
FIG. 10 is an isometric view of a buckle that is another embodiment of an aspect of the invention disclosed herein, showing the buckle latched in an engaged condition, as after a predetermined tension has been applied to the buckle by the strap portion of the pelvis-stabilizing device.
Figure 11:
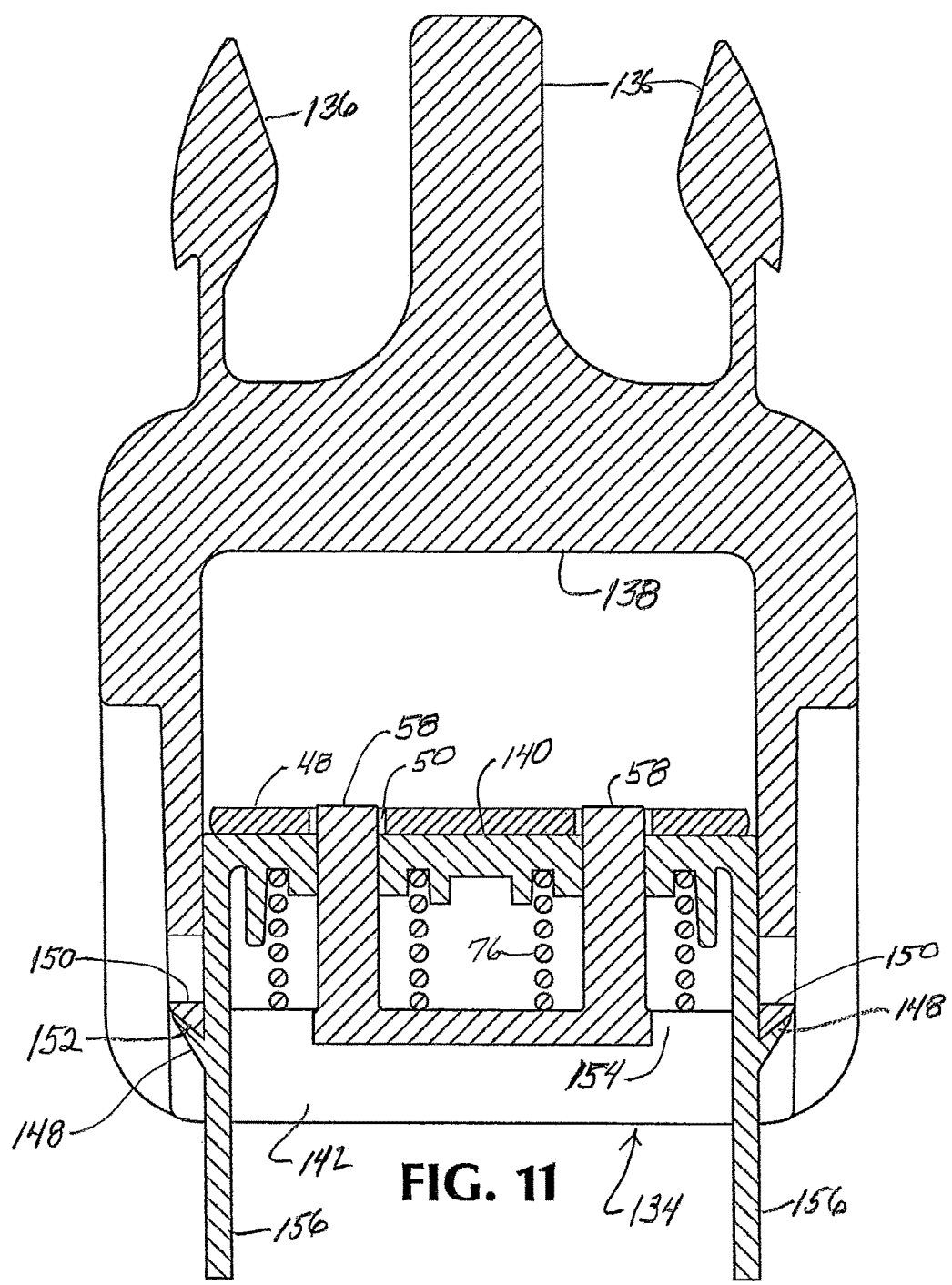
FIG. 11 is a sectional view of the buckle shown in FIG. 10, taken along line 11-11 of FIG. 10, showing the buckle latched in an engaged condition.
Figure 12:
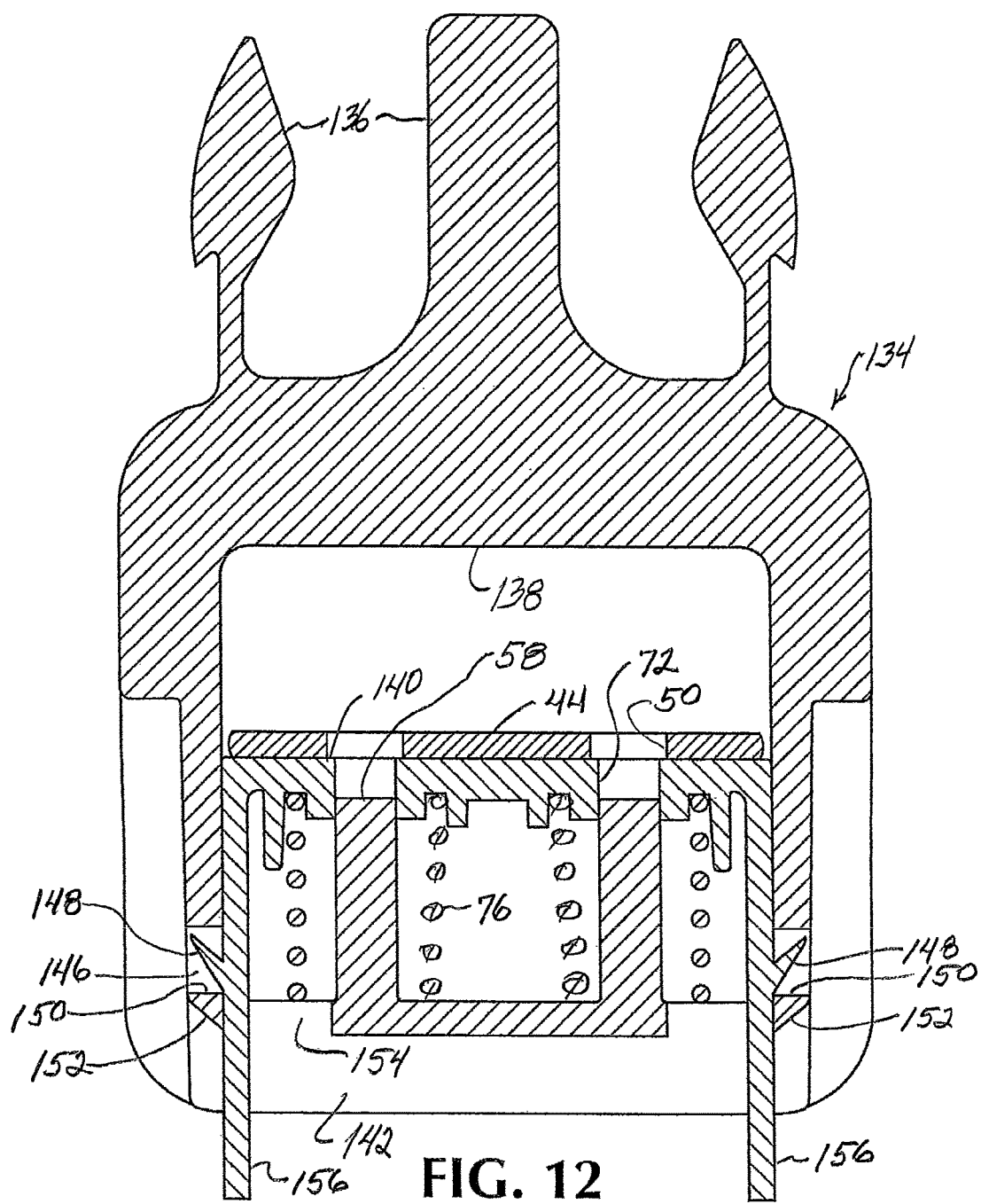
FIG. 12 is a view similar to FIG. 11, showing the condition of the buckle when disengaged, as before being subjected to a predetermined tension in the strap that is part of the pelvis-stabilizing device shown in FIGS. 1-3.
Figure 13:
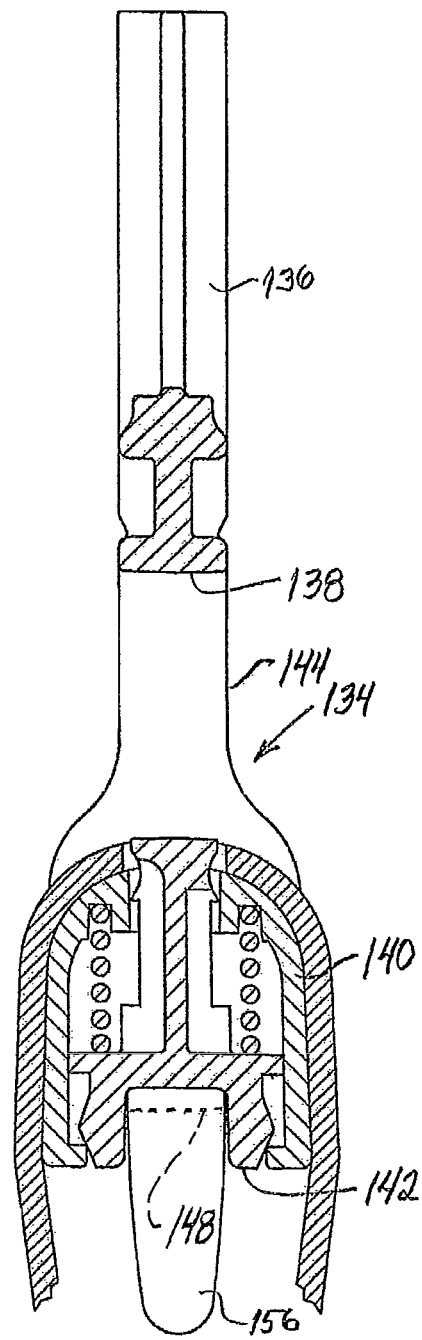
FIG. 13 is a sectional view of the buckle shown in FIG. 10, taken along line 13-13 of FIG. 10, with the buckle in the state in which it is shown in FIG. 10.
Figure 14:
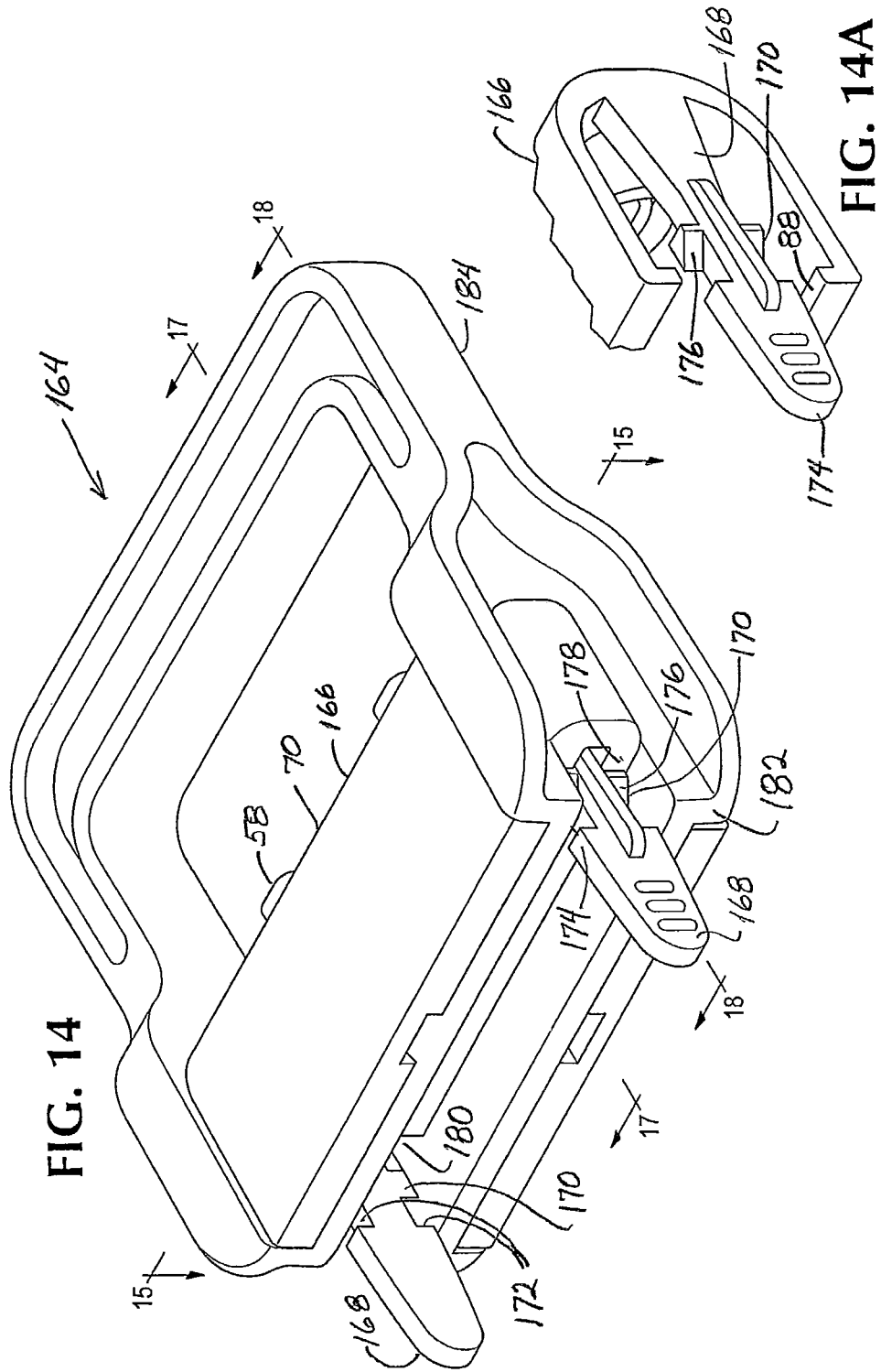
FIG. 14 is an isometric view of a buckle that is a third embodiment of an aspect of the invention disclosed herein.
Figure 15:
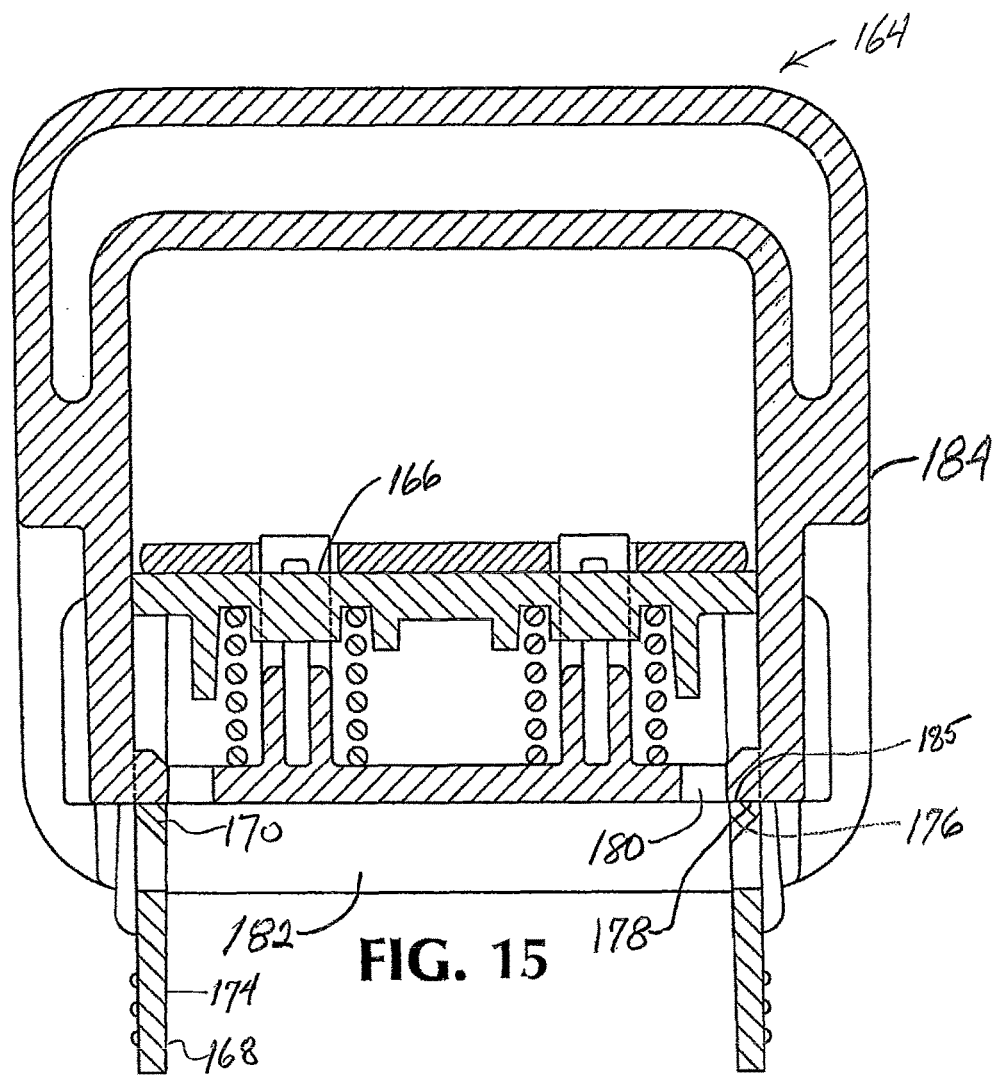
FIG. 15 is a sectional view of the buckle shown in FIG. 14, taken along line 15-15 of FIG. 14, showing the buckle latched in an engaged condition, as when subjected to a predetermined tension to cause the buckle to engage a hole defined in the strap that is part of the pelvis-stabilizing device shown in FIGS. 1-3.

A respective retaining flange 78 extends along the base 74 on each of the opposite sides 80 and 82 side of the frame 60, and each of the corresponding opposite sides 84 and 86 of the slider 62 includes an inwardly directed retaining lip 88 that engages the respective flange 78 and keeps the slider 62 from moving toward the bow 64 from the position shown in FIG. 8, thus keeping the springs compressed. The slider 62 may be molded or otherwise formed from a suitable elastic material such as a resilient and tough but generally rigid plastics material so that the opposite sides 84 and 86 of the slider can be sprung apart from each other as the slider is moved into position within the opening defined by the frame, with the lips 88 passing over the flanges 78 to reach the position shown in FIG. 8.

Figure 4:
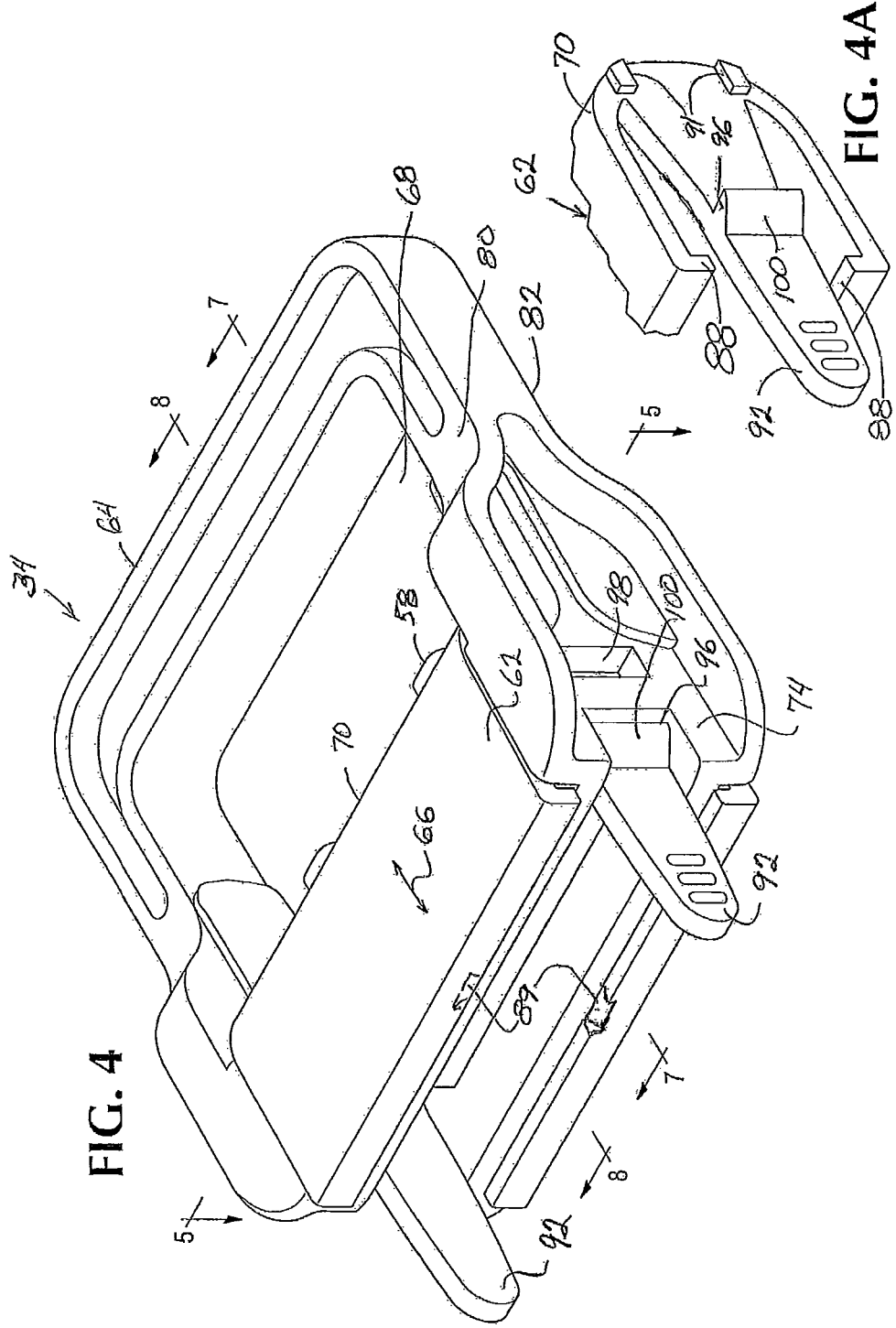
FIG. 4 is an isometric view of a buckle that is one embodiment of the buckle included in the pelvis-stabilizing device shown in FIG. 1 at an enlarged scale.
Figure 6:
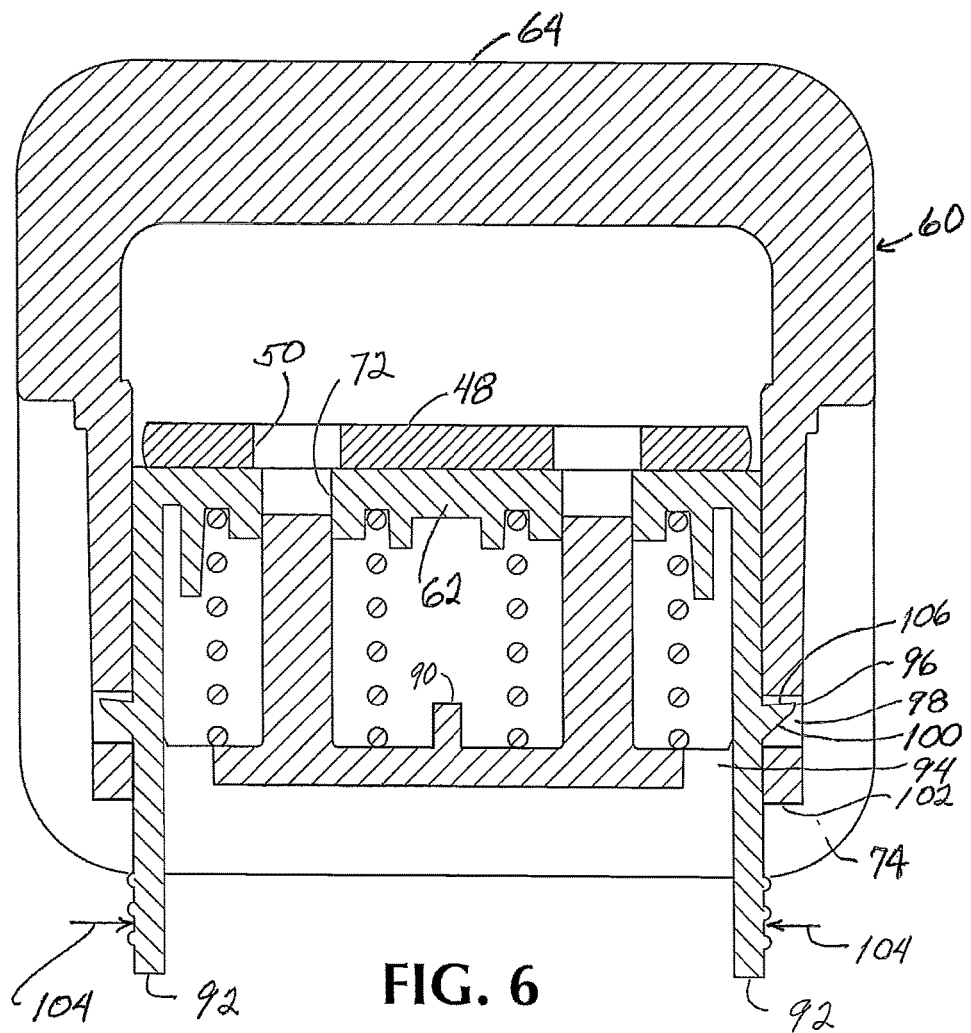
FIG. 6 is a sectional view of the buckle, similar to FIG. 5, showing the condition of the buckle before tension has been applied to the buckle by the strap portion of the pelvis-stabilizing device.

To assist in placing the slider 62 in the position with respect to the frame 60 shown in FIG. 4, an assembly cam 90 may be provided on the base 74 of the buckle frame 60 in position to engage the interior of the slider 62 and force the opposite side portions 86 and 88 of the slider 62 apart from each other as the slider 62 is moved within the frame 60 toward the base 74. The assembly cam 90 thus forces the lips 88 far enough apart so that they can pass over the flanges 78 allowing the slider 62 to move to the position in which the lips can return toward the base 74 and engage the flanges as shown in FIGS. 6 and 8. A notch 89 may be provided in one or both of the lips 88 to initially receive the assembly cam 90 and align the slider 62 with the base 74 as the slider 62 is moved into place.

Substantial tension must be applied to the buckle 34 in use, urging the slider 62 to move in opposition to the springs 76 before the slider 62 begins to move relative to the buckle frame 60. As may be seen in FIG. 4A, a pair of guide blocks 91 may engage a portion of the frame 60 to keep the slider 62 properly aligned with the buckle frame 60.

Once sufficient tension is provided in the strap 44, urging the buckle away from the first end portion 36 of the main body portion of the pelvic sling 30, as the strap 44 is moved further along the convex contact surface 70 of the slider 62, a pair of holes 50 in the strap 44 will move into alignment with the holes 72 in the slider 62. This will allow the pins 58 to enter into the holes 50 in the strap 44 as the slider 62 compresses the springs 76 further and moves along the pins 58 toward the base 74 of the frame 60.

Figure 5:
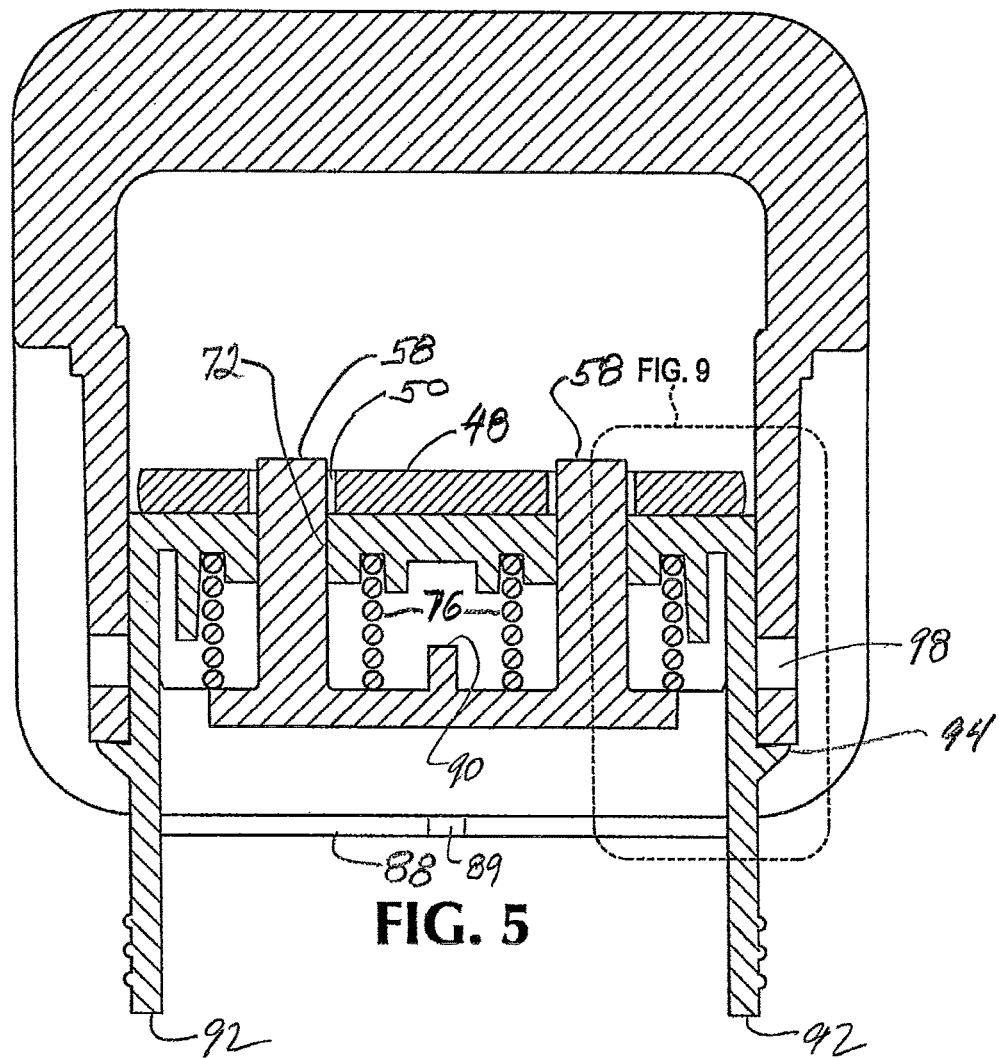
FIG. 5 is a sectional view of the buckle shown in FIG. 4, taken along line 5-5 of FIG. 4, showing the buckle in an engaged condition, when subjected to a predetermined tension to cause the buckle to engage a hole defined in the strap that is part of the pelvis-stabilizing device shown in FIGS. 1-3.

As may be seen by reference to FIGS. 4A, 5, and 6, a pair of latch fingers 92 extends from the interior of the slider 62, parallel with the sides of the frame 60 and toward the base 74 of the frame. The latch fingers 92 extend through correspondingly located through-holes 94 in the base of the frame, and outer ends of the latch fingers 92 are exposed beyond the base 74 of the frame 60. Each of the latch fingers 92 carries a catch 96 that extends laterally outward toward a respective end of the frame 60. When the slider 72 is in its unengaged, or first, position, as shown in FIGS. 6 and 8, each catch 96 extends into a receptacle that may be in the form of an opening 98 extending through the respective end of the frame. The latch fingers 92 when relaxed may be oriented in slightly divergent directions and thus under small amount of pressure and slightly flexed toward each other inward when the slider 62 is in its relaxed first position with respect to the frame 60 as shown in FIG. 6, in which the catches are received in the receptacles 98. Each catch 96 may have an inclined cam surface 100, facing away from the convex strap contact face 70 of the slider 62 and thus generally toward the base or outer end of the frame 60.

As the slider 62, urged by the strap 44, moves from the position shown in FIG. 6 toward the base portion 74 of the frame 60, the cam surface 100 engages and rides upon the lower margin of the receptacle 98, and the cam 100 forces the latch finger 92 inward, disengaging the catch 96 from the receptacle 98 and allowing the catch 96 to ride along a surface extending generally longitudinally of the frame as shown in FIG. 9B. When the slider 62 has moved a desired distance, far enough to expose the tips of the pins 58 far enough to extend into the holes 50 in the strap 44 and to engage the strap 44 securely to accept and bear the longitudinal forces in the strap, each catch 96 can be moved elastically by the respective latch finger 92 to move beneath the bottom of the frame and engage a latch strike surface 102 at the bottom of the frame locking receptacle. With the catches 96 engaged with the latch strike surfaces 102, the slider 62 is no longer free to move under the influence of the springs toward the position shown in FIG. 6 and thus hide the tips of the pins 58 and allow the strap 44 to slide along the convex strap contact face 70 of the slider 62. This makes it easier for a person placing the pelvic sling 30 on a patient to secure the portion of the strap 44 extending beyond the buckle 34 to the first end portion 36, using the hook-and-loop fastener materials 54 and 56 previously described, or by some other means.

When it is desired to release the pelvic sling 30 from a patient, the two latch fingers 92 can be squeezed together as indicated by the arrows 104 in FIG. 6, which results in the catches 96 being withdrawn from their respective latch strike surfaces 102. Once the slider 62 can move at least a slight distance, the tips of the catches 96 will be able to move along the frame as shown in FIG. 9B toward the bow 64 of the frame 60. The slider 62 will then be able to move toward its original, relaxed position with respect to the bow of the frame 60 once tension in the strap 44 is reduced, as by disengaging the hook-and-loop fastener materials 54 and 56 from each other. The slider 62 will then move to the position shown in FIGS. 6 and 8 and the strap 44 will then be able to again slide along the convex strap contact surface 70 within the frame 60.

As may be seen in FIG. 9A, the catch 96 may have an engagement face 106 defining an acute angle 108 with the fingers 92 to account for flexibility of the finger 92 and thus result in contact of the engagement face 106 against the latch strike surface 102, rather than a tendency to act as a cam and move the finger 92 in the direction of the arrow 104.

Referring next to FIGS. 10-13, a buckle 134 is generally similar to the buckle 34. The buckle 134 has, as shown herein, a set of prongs 136 of the male member of a side release buckle; extending from the bow portion 138, of the frame 60, and the configuration and interrelationship between the slider 140 and the base portion 142 of the frame 144 are slightly different. A corresponding female part of a side release buckle (not shown) may be fastened to the first end portion 36 of a main body portion 32 of a pelvic sling 30 by a loop 38, to receive the prongs 136, and attach the buckle 134 to the main body portion 32. In the buckle 134 as shown in FIGS. 10-13, there are receptacles 146 for the catches 148 on the respective sides of the base portion 142 of the frame 144, and a crossbar 150 on each side of the frame 144 includes a strike face 152. The through-holes 154 in the base of the frame 144 give ample room for the fingers 156 to be squeezed toward each other in the directions of the arrows 157, to release the catch 148 from the respective latch strike face 152 on each end. As shown best in FIG. 13, the strike face and the catch are oriented at an angle 158 to assure that, even allowing for some flexing of the fingers 156 caused by the forces generated in the springs, the catches 148 tend to remain engaged with the strike faces 152 and not to be cammed out of engagement with one another.

Referring next to FIGS. 14-18, a buckle 164, like the buckle 134, is generally similar to the bucket 34. In the buckle 164, the slider 166 has a pair of fingers 168, but instead of each finger 168 having an outwardly projecting catch with a cam surface, the fingers 168 are generally flat-sided on both of their inner and outer faces. Each finger 168 has a crossbar 170 that may define a pair of notches 172 between the crossbar 170 and a wide distal end part 174. As may be seen best in FIG. 18, a lower cam surface 176 of each crossbar 170 may be inclined so as to be able to act as a cam against a respective latch strike member, to cause the respective finger 168 to flex inwardly when the slider 166 is forced downward toward the base 182 by tension in the buckle 164 and strap 44. Each finger 168 extends through a respective through-hole 180 in the base 182 of the frame 184. Respective catch engagement faces 185, which may be substantially perpendicular to the respective finger 168 and generally parallel with the base 182 of the frame 184, can engage each latch strike member 178 when the slider 166 has moved far enough to allow the finger 168 to enter the notch in the latch strike 178. Once the catch faces 185 have engaged the latch strike faces 178, the slider 166 is retained in its lowered position with the tips of the pins 58 exposed beyond the convex strap contact 70 surface and engaged in the holes 50 in the strap 44 as described in greater detail above with respect to the buckle 34 and with respect to the pelvic sling 30 as illustrated in FIGS. 1,2, and 3.

Figure 16:
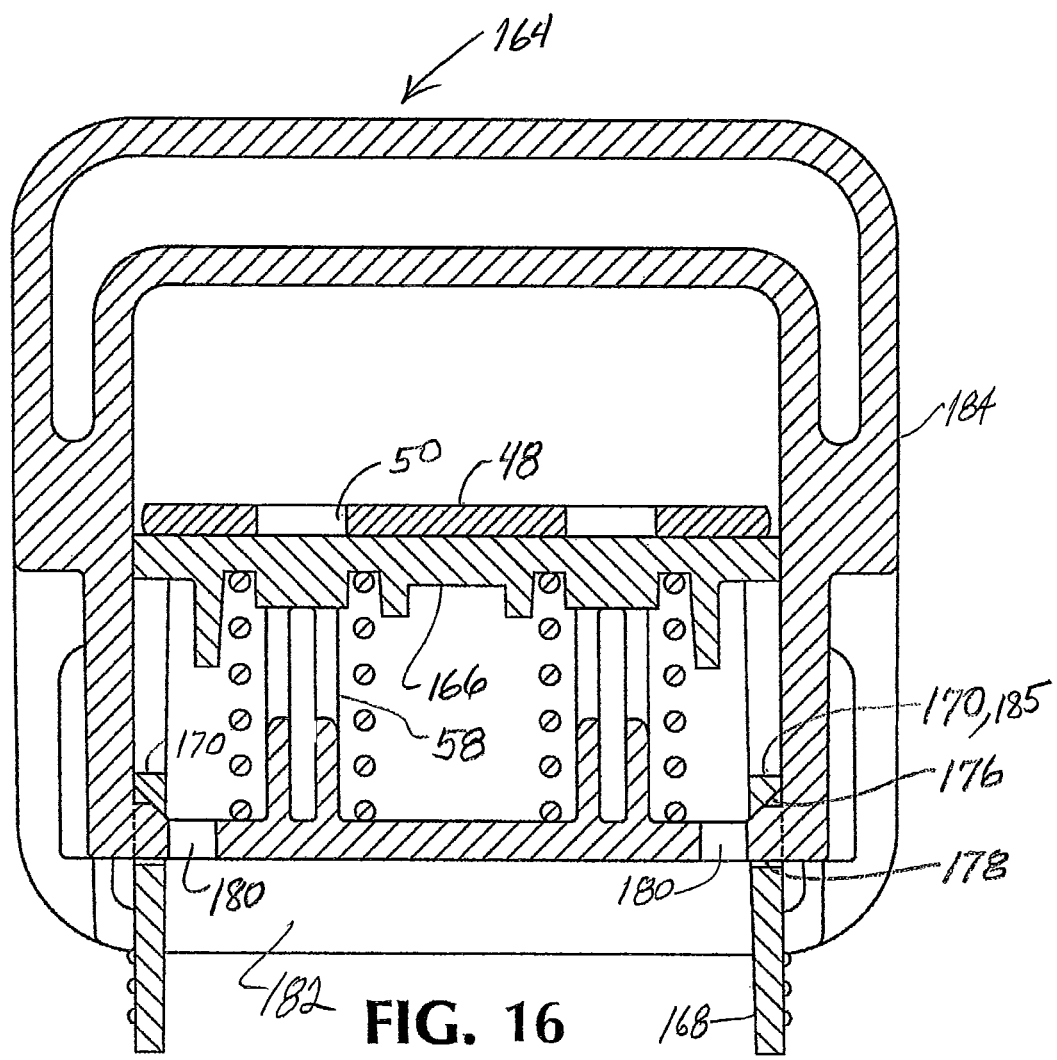
FIG. 16 is a view similar to FIG. 15, but showing the condition of the buckle before tension has been applied to the buckle by the strap portion of the pelvis-stabilizing device.
Figures 17, 18:
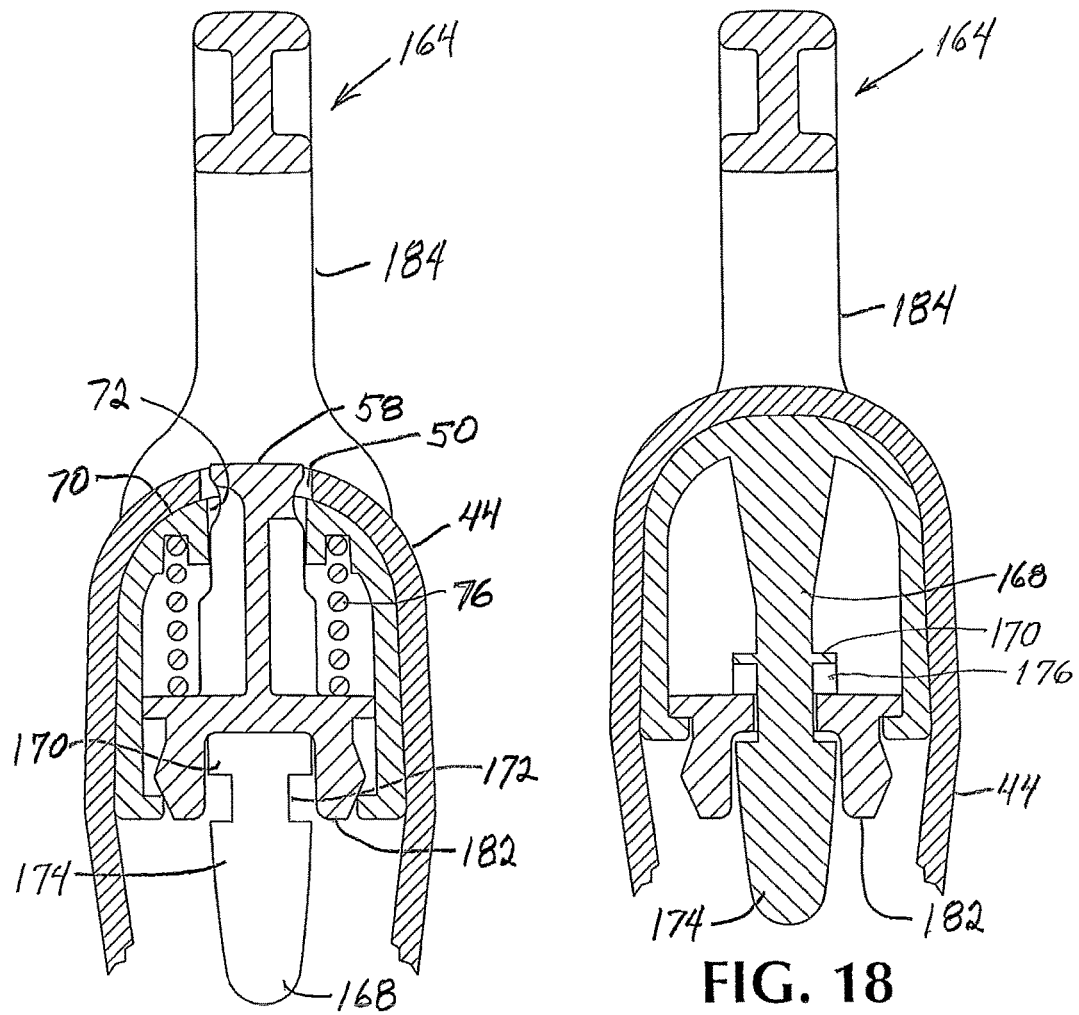
FIG. 17 is a sectional view of the buckle shown in FIG. 14, taken along line 17-17 of FIG. 14, with the buckle in the state in which it is shown in FIGS. 14 and 15.
FIG. 18 is a sectional view taken along line 18-18 of FIG. 14, with the buckle shown in the state it is in as shown in FIG. 16.
Figure 19:
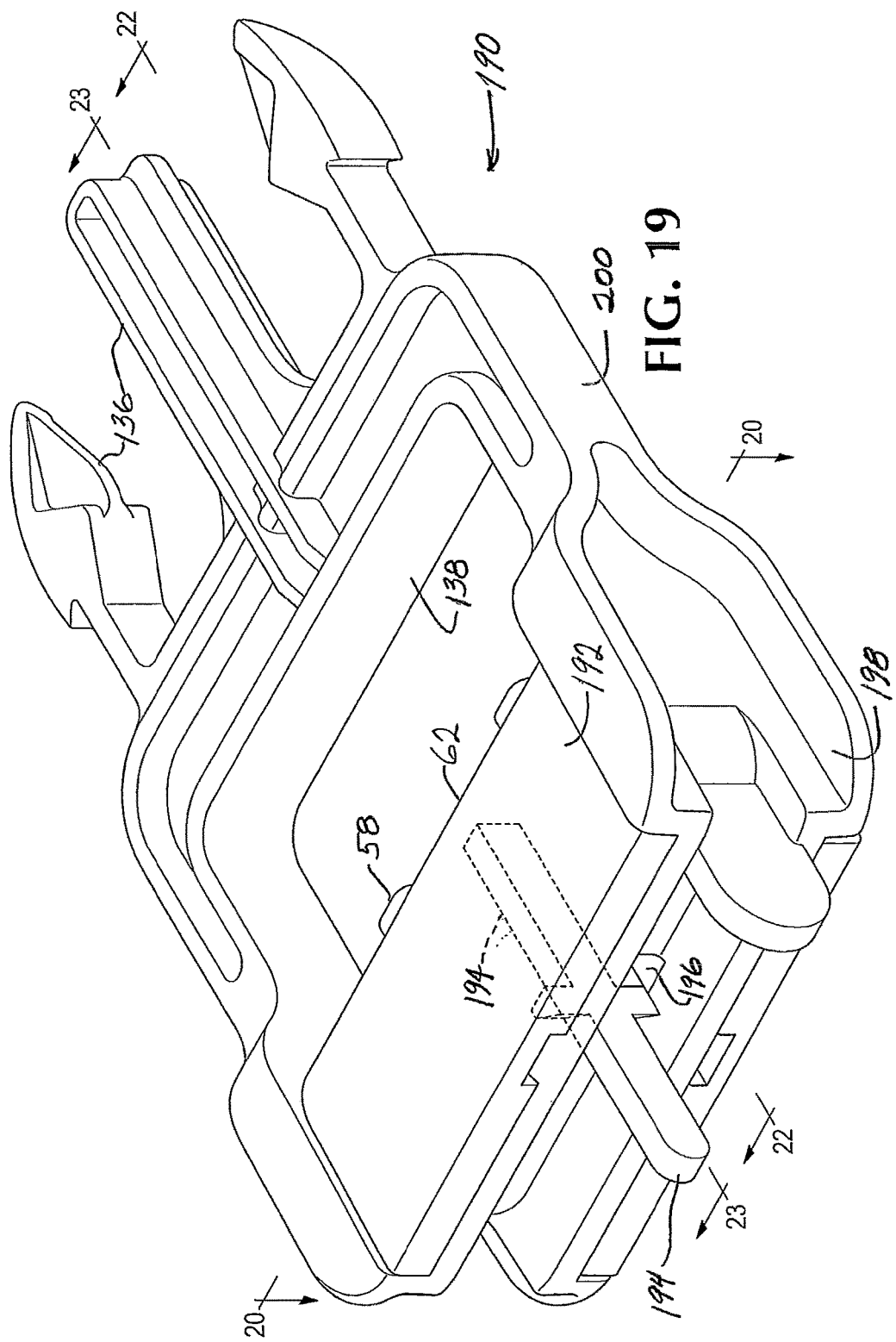
FIG. 19 is an isometric view of a buckle that is yet another embodiment of an aspect of the invention disclosed herein.
Figure 20:
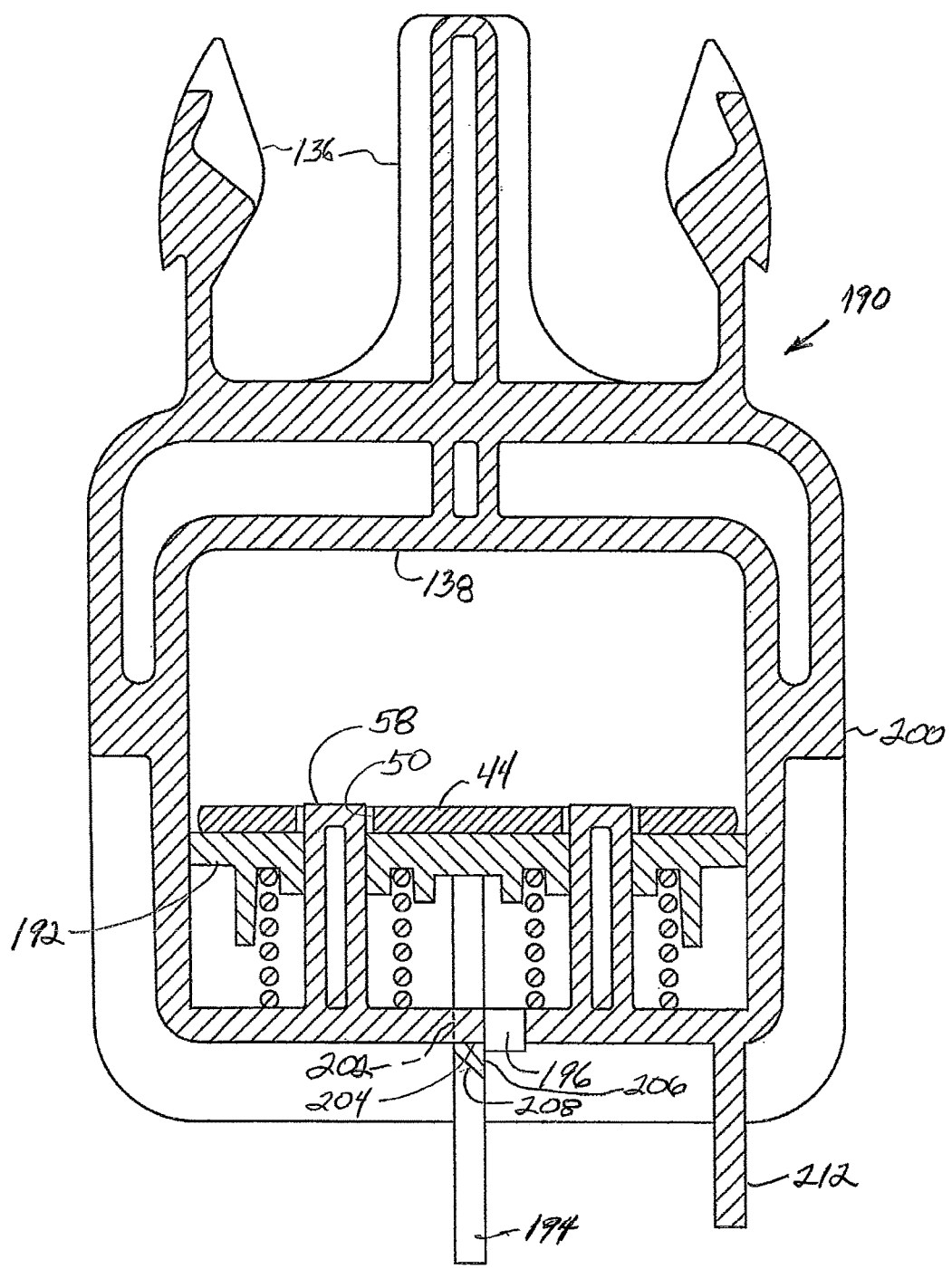
FIG. 20 is a sectional view of the buckle shown in FIG. 19, taken along line 20-20, showing the buckle latched in an engaged condition, as when subjected to a predetermined tension to cause the buckle to engage a hole defined in the strap that is part of the pelvis-stabilizing device shown in FIGS. 1-3.
Figure 21:
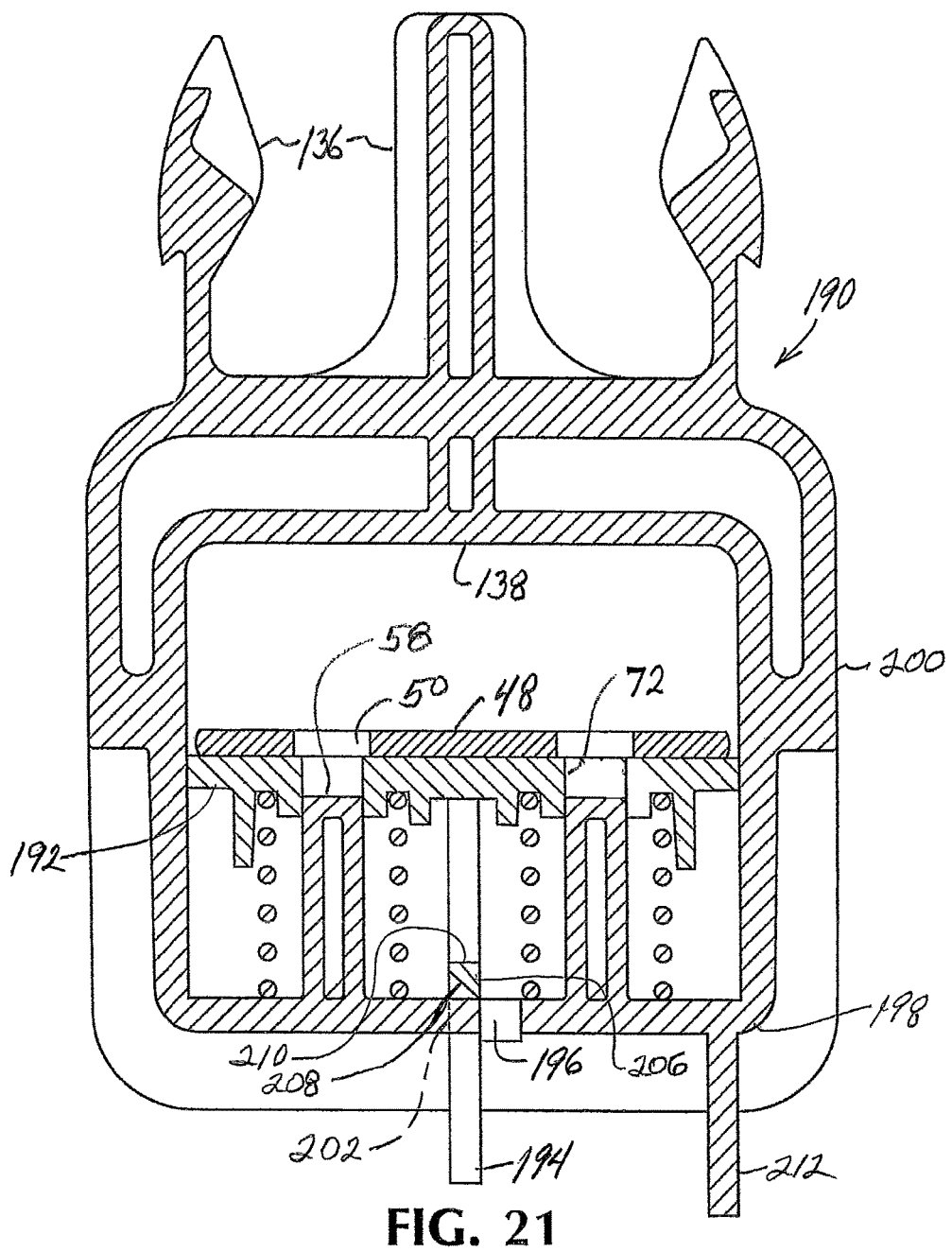
FIG. 21 is a view similar to FIG. 20, showing the buckle in an unengaged state, as before tension has been applied to the buckle by the strap portion of the pelvis-stabilizing device shown in FIGS. 1-3.
Figure 22:
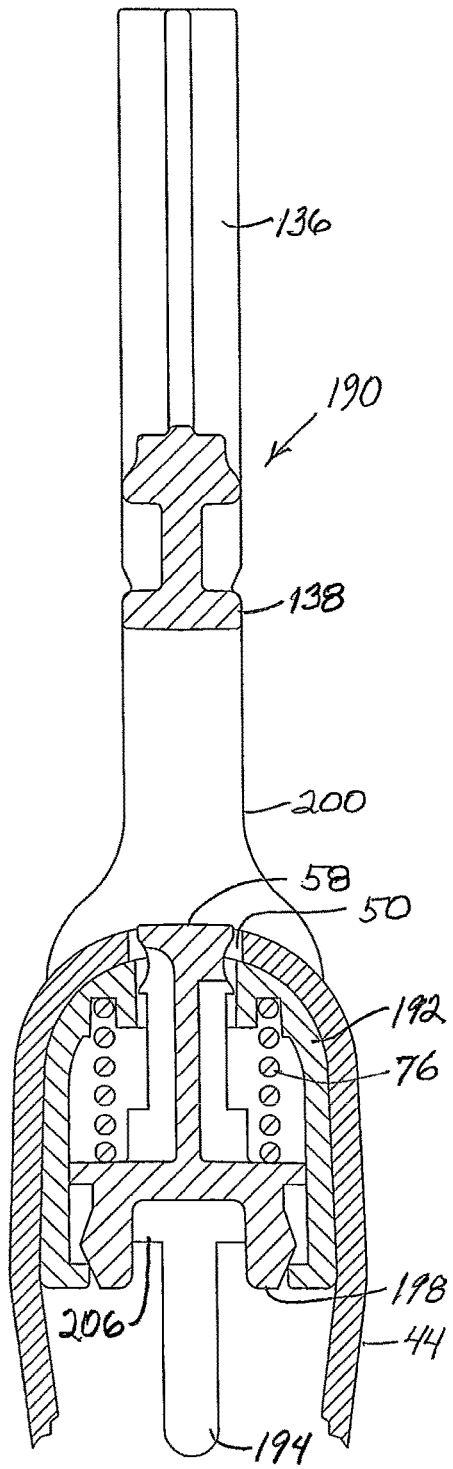
FIG. 22 is a sectional view of the buckle shown in FIG. 19, taken along line 22-22 of FIG. 19, with the buckle in the state in which it is shown in FIGS. 19 and 20.
Figure 23:
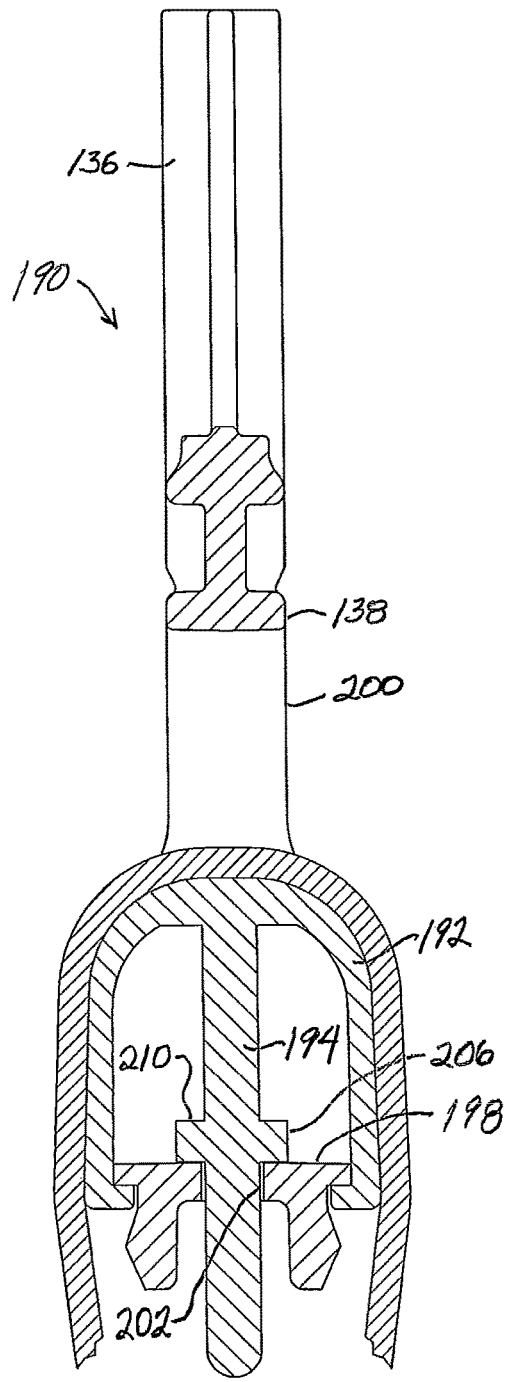
FIG. 23 is a sectional view taken along line 23-23 of FIG. 19, showing the buckle in the unengaged state in which it is shown in FIG. 21.
Figure 24:
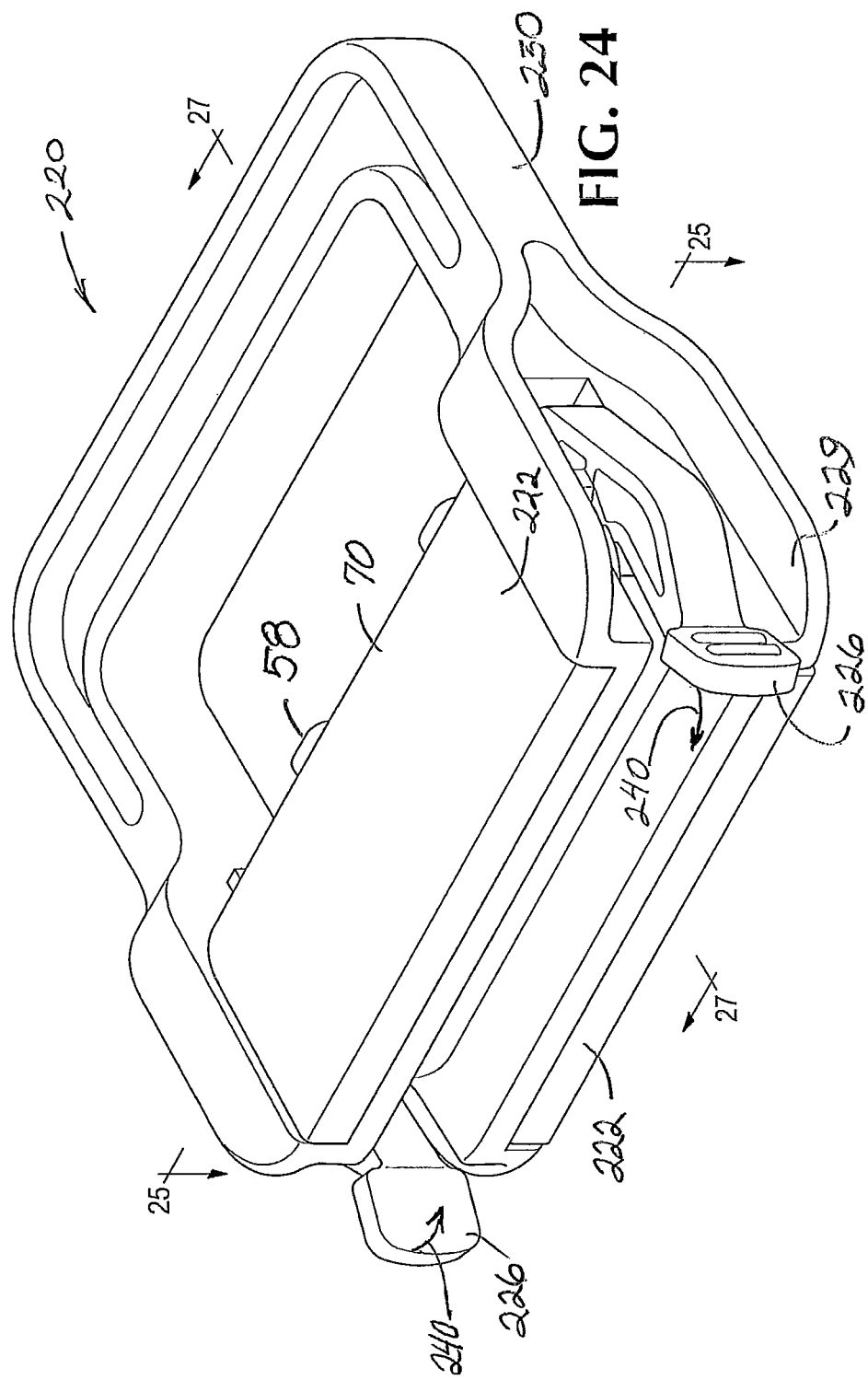
FIG. 24 is an isometric view of a buckle that is yet another embodiment of the buckle incorporated in the device shown in FIGS. 1-3.

As shown in FIGS. 19-23, a buckle 190 is similar in many respects to the buckle 164 shown in FIGS. 14-18, but instead of having a pair of flexible fingers extending from the slider 192, only a single, centrally located finger 194 is provided. The finger 194 extends through a centrally located through-hole 196 in the base 198 of the buckle frame 200, where a notch 202 is defined at one side of the through-hole 196 and defines strike faces 204. Extending on at least one side and shown on both sides of the finger 194 as shown in FIGS. 16-18, a crossbar 206 includes a cam surface 208 and latching surface 210 similar to those of the fingers 168 in the previously described buckle 164.

To assist in unlatching the slider from the latched, or engaged, position of the slider, a thumb rest 212 is provided on one side of the base portion 198, facilitating flexing of the finger 194 to disengage the latch and release the slider 192 to move toward the bow end of the frame. The thumb rest 212 also provides a definite indication of which way the finger 194 has to be moved to release it from engagement in the notch 202.

Figure 25:
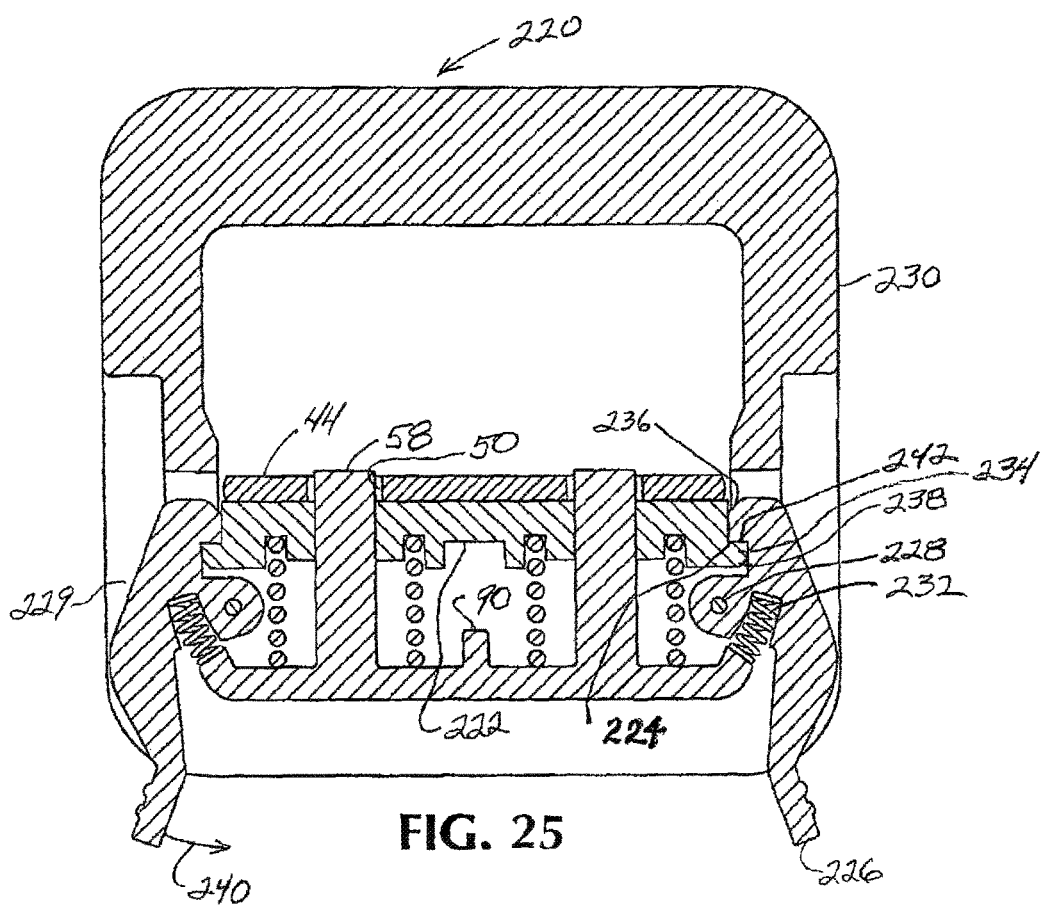
FIG. 25 is a sectional view taken along line 25-25 of FIG. 24, showing the buckle latched in an engaged state.
Figure 26:
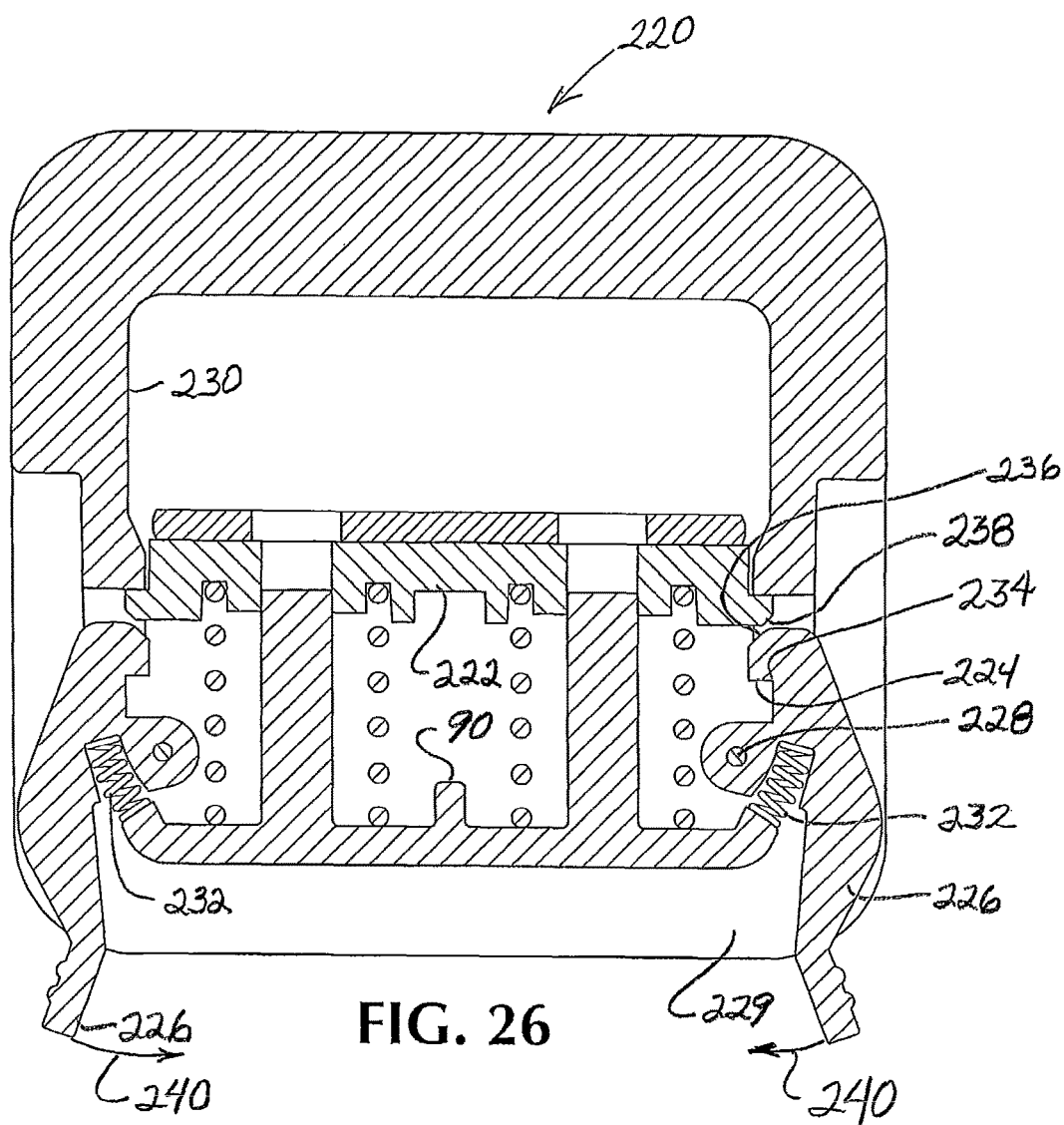
FIG. 26 is a view similar to FIG. 25, showing the buckle in an unengaged state, as before tension has been applied to the buckle by a strap portion of the pelvic stabilizing device showns in FIGS. 1-3.
Figures 27, 28:
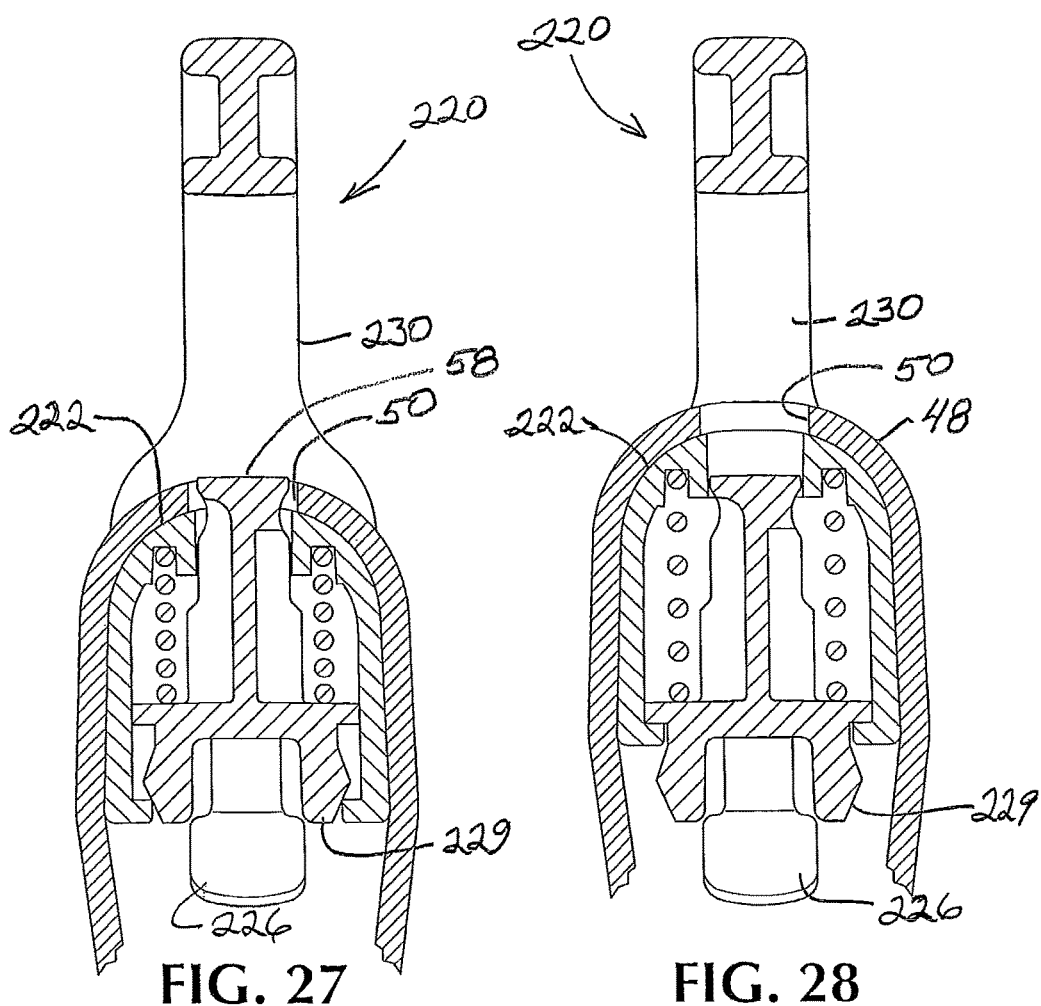
FIG. 27 is a sectional view taken along line 27-27 of FIG. 24, showing the buckle in the state in which it is shown in FIG. 25.
FIG. 28 is a sectional view similar to FIG. 27, but showing the buckle in the state in which it is shown in FIG. 26.

Yet another generally similar buckle 220 is shown in FIGS. 24-31, where the slider 222 is latched in its latched, strap-engaging, second position state by a pair of catches 224 carried on respective latch levers 226. Each latch lever 226 is mounted on a pivot pin 228 on the base portion 229 of the frame 230 and biased, as by a spring 232, toward a position in which a catch 224 carried on the latch lever 226 can engage a corresponding latch strike member 234 carried on the slider 222, once the slider 222 has been moved, as by tension in a strap 44, to a strap-engaging position in which the pins 58 protrude from the convex strap contact face 70 of the slider 222. At least one of the latch strike member 234 and the catch 224 portion of the latch lever 226 may include a cam surface as shown at 236 and 238, so that as the slider 222 is moved from its original, relaxed, pre-installation position as shown in FIG. 26 toward the latched strap-engaging state shown in FIGS. 24 and 25, the cam 236 or cams 236 and 238 will move the catch 224, causing the lever 226 to pivot in a first direction as indicated by the arrow 240 to allow the catch 224 to pass by the latch strike member 234. Once the slider 222 has moved to the strap-engaging second position shown in FIGS. 24, 25, and 27, the latch lever spring 232 causes the lever 226 to pivot in the direction opposite that indicated by the arrow 240, to move the catch 224 into engagement with the latch strike face 242 of the strike member 234. The catch 224 then retains the slider 22 in the latched engagement position as shown best in FIGS. 25 and 27.

The position of the pivot pin shown in FIG. 25 is designed, with respect to the frame 230, and with respect to the selected spring 223, so as preferably to require a force in the direction of the arrow 240 amounting to about 6 pounds, to move the lever 226 and thus disengage the catch 224 from the latch strike member 234. The latch lever 226 may be made of a suitably strong synthetic plastic resin or of a metal such as an aluminum or steel alloy.

The terms and expressions that have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A buckle, comprising:
   (a) a frame having a base portion and a pair of opposite sides and defining an opening through the frame from one to the other of the opposite sides;
   (b) an engagement member mounted on and extending from the base portion of the frame;
   (c) a movable member disposed within the opening adjacent the base and movable between a first portion with respect to the frame, in which the movable member hides the engagement member, and a second position with respect to the frame, in which at least a portion of the engagement member is exposed with respect to the movable member;
   (d) an elastic member urging the movable member toward the first position; and
   (e) a latch mechanism arranged to be engaged automatically in response to the movable member moving into the second position, the latch mechanism being adapted to hold the movable member in the second position with respect to the frame when the latch mechanism is engaged, and the latch mechanism being capable of holding the movable member in the second position without assistance from a strap, and thus being capable of preventing the elastic member from moving the movable member from the second position.

2. The buckle of claim 1, wherein the elastic member is a spring that provides a predetermined force holding the movable member in the first position.

3. The buckle of claim 1, wherein the movable member is a slider having a strap contact face, and wherein the frame and the slider together define a passageway adapted to receive the strap extending from one to the other of the opposite sides of the frame and along and in contact with the strap contact face of the slider.

4. The buckle of claim 3, wherein the slider defines a through-hole and the engagement member is a pin mounted on the base portion of the frame and aligned with the through-hole in the slider, the pin protruding proud of the strap contact face of the slider when the slider is in the second position with respect to the base portion of the frame.

5. The buckle of claim 3, wherein:
   the base portion of the frame defines a through hole;
   the slider includes a finger extending through the through-hole;
   the finger includes a protruding catch;
   the base portion includes a latch strike surface located where it can be engaged by the catch when the slider moves into the second position with respect to the base portion; and
   the finger is elastically biased to urge the catch into engagement with the latch strike surface.

6. The buckle of claim 5, including a pair of said fingers extending from the slider and spaced apart from one another, at least one of the fingers being elastically biased apart from the other and the fingers extending from the base portion of the frame when the movable member is in the second position and the latch mechanism is engaged, and wherein the latch mechanism can be disengaged by moving the fingers toward each other.

7. The buckle of claim 5, wherein the finger has a relatively wide distal end portion and a relatively narrow neck portion, the catch extends from a side of the finger and has a cam on a distal side of the catch, the through-hole being large enough to permit passage of the finger and the catch therethrough, and wherein the base portion of the frame defines a notch adjacent to and communicating with the through-hole, the notch being too small to permit passage of the distal end portion of the finger and the catch therethrough; the base portion of the frame defining a latch strike surface adjacent the notch; and the finger being elastically biased toward the notch and the slider being aligned with respect to the frame so that when the slider is in the second position the finger is within the notch and the catch is engaged with the latch strike surface.

8. The buckle of claim 1 wherein the base portion of the frame includes a protruding retainer flange on each of the opposite sides of the frame; wherein the movable member is a slider including a pair of opposite side portions each corresponding to a respective one of the opposite sides of the frame;
   wherein each of the opposite side portions of the slider includes a respective inwardly-directed retainer lip located facing an exterior side of the respective flange so as to keep the slider in place on the frame; wherein the slider is of an elastic material flexible and is resilient enough for the opposite side portions of the slider to be separated from each other far enough for the retainer lips to pass over the retainer flange and thereafter to keep the retainer lips in position to engage the retainer flange; and wherein the base portion of the frame includes an assembly cam located on an interior face of the base portion, where the assembly cam will urge the opposite side portions of the slider apart from each other far enough for the retainer lips to pass over and engage the retainer flanges as the slider is being mounted on the base portion during assembly of the buckle.

9. The buckle of claim 8 wherein each of the opposite side portions of the slider defines a notch arranged to receive the assembly cam and align the slider with the base portion of the frame as the slider is being mounted onto the base portion.

10. The buckle of claim 1 wherein the latch mechanism includes a lever mounted pivotally on the frame, a catch carried on the lever, and a latch lever spring interconnected with the frame and urging the lever toward a position in which the catch engages a corresponding latch strike carried on the movable member.

11. The buckle of claim 10 wherein at least one of the catch and the latch strike includes a cam and wherein the cam causes the lever to pivot in a first direction with respect to the frame, to a position in which the catch can pass over the latch strike as the movable member moves from the first position to the second position, and wherein the latch lever spring urges the lever to pivot in an opposite direction, thereby engaging the catch with the latch strike once the movable member has reached the second position.

12. A pelvic binding system, comprising:
(a) an elongated main body portion having opposite first and second end portions;
(b) a buckle attached to said first end portion of said main body portion;
(c) a flexible elongate strap having an inner end attached to said second end portion, the strap extending away from said main body portion and having an outer end portion opposite from said inner end thereof, the strap being of a size to pass through the buckle and the buckle being adapted to engage the strap so as to interconnect the first and second end portions of the main body portion with each other, the strap having an area of flexible fastener material of a first kind located on a first side of the strap;
(d) an area of flexible fastener material of a second kind that is cooperatively matable with the flexible fastener material of the first kind, located on the second end portion of the main body portion;
(e) and wherein the buckle comprises:
(i) a frame having a base portion and a pair of opposite sides and defining an opening through the frame from one to the other of the opposite sides;
(ii) an engagement member mounted on and extending from the base portion of the frame;
(iii) a movable member disposed within the opening adjacent the base and movable between a first position with respect to the frame, in which the movable member hides the engagement member, and a second position with respect to the frame, in which at least a portion of the engagement member is exposed with respect to the movable member;
(iv) an elastic member urging the movable member toward the first position; and
(v) a latch mechanism arranged to be engaged automatically in response to the movable member moving into the second position, the latch mechanism being adapted to hold the movable member in the second position with respect to the frame when the latch mechanism is engaged, and the latch mechanism. being capabale of holding the moveable member in the second position without assistance from the strap and thus being capable of preventing the elastic member from moving the movable member from the second position.

13. The buckle of claim 12 wherein the elastic member provides a predetermined force acting on the movable member and urging the movable member to remain in the first position when the movable member is in the first position.

14. The pelvic binding system of claim 12, wherein the movable member is a slider having a strap contact face, and wherein the frame and the slider together define a passageway adapted to receive the strap extending along and in contact with the strap contact face of the slider.

15. The pelvic binding system of claim 14, wherein the slider defines a through-hole and the engagement member is a pin mounted on the base portion of the frame and aligned with the through-hole in the slider, the pin protruding proud of the strap contact face of the slider when the slider is in the second position with respect to the base portion of the frame.

16. The pelvic binding system of claim 15, including a pair of the fingers extending from the slider and spaced apart from one another, at least one of the fingers being elastically biased apart from the other and the fingers being arranged to extend from the base portion of the frame when the latch is engaged, and wherein the latch can be disengaged by moving the fingers toward each other.

17. The pelvic binding system of claim 12, wherein:
(a) the base portion of the frame defines a through-hole;
(b) the movable member is a slider that includes a finger extending through the through-hole;
(c) the finger includes a protruding catch;
(d) the base portion includes a strike surface located where it can be engaged by the catch when the slider moves into the second position with respect to the base portion; and
(e) the finger is elastically biased to urge the catch into engagement with the latch strike surface.

18. The pelvic binding system of claim 16, wherein the finger has a relatively wide distal end portion and a relatively narrow neck portion, a catch portion extending from a side of the finger and having a cam on a distal side of the catch, the base portion of the frame defining a through hole large enough to permit passage of the finger and the catch therethrough, and the base portion of the frame defining a notch adjacent to and communicating with the through hole, the notch being too small to permit passage of the finger and the catch therethrough, and the base portion of the frame defining a latch strike surface adjacent a side of the notch and the finger being elastically biased toward the notch and the slider being aligned with respect to the frame so that when the slider is in the second position the finger is within the notch and the catch is engaged with the latch strike surface.

19. The pelvic binding system of claim 12, wherein the base portion of the frame of the buckle includes a protruding retainer flange on each of the opposite sides of the frame; wherein the movable member is a slider including a pair of opposite side portions each corresponding to a respective one of the opposite sides of the frame; wherein each of the opposite side portions of the slider includes a respective inwardly-directed retainer lip located facing an exterior side of the respective retainer flange so as to keep the slider in place on the frame; wherein the slider is of an elastic material flexible and is resilient enough for the opposite side portions of the slider to be separated from each other far enough for the retainer lips to pass over the retainer flange and thereafter to keep the retainer lips in position to engage the retainer flange; and wherein the base portion of the frame includes an assembly cam located on an interior face of the base portion, where the assembly cam will urge the opposite side portions of the slider apart from each other far enough for the retainer lips to pass over and engage the retainer flanges as the slider is being mounted on the base portion within the opening defined by the frame during assembly of the buckle.

20. The pelvic binding system of claim 19 wherein each of the side portions of the slider defines a notch arranged to receive the assembly cam and keep the slider aligned with the base portion of the frame as the slider is urged onto the base portion.

21. The pelvic binding system of claim 12 wherein the latch mechanism includes a lever mounted pivotally on the frame, a catch carried on the lever, and a latch lever spring interconnected with the frame and urging the lever toward a position in which the catch engages with a corresponding latch strike member carried on the moveable member.

22. The pelvic binding system of claim 21 wherein at least one of the catch and the latch strike member includes a cam and wherein the cam causes the lever to pivot in a first direction with respect to the frame, to a position in which the catch can pass over the latch strike member as the movable member moves from the first position to the second position, and wherein the latch lever spring urges the lever to pivot in an opposite direction, thereby engaging the catch with the latch strike member once the movable member has reached the second position.

* * * * *

UNITED STATES PATENT AND TRADEMARK OFFICE
CERTIFICATE OF CORRECTION

PATENT NO. : 10,182,934 B2
APPLICATION NO. : 14/097018
DATED : January 22, 2019
INVENTOR(S) : Lance David Hopman et al.

Page 1 of 1

It is certified that error appears in the above-identified patent and that said Letters Patent is hereby corrected as shown below:

In the Specification

Column 6, Line 31: Change "FIG. 8" to read "FIGS. 3 and 4"

In the Claims

Column 12, Line 5 Claim 12: Delete the "." between "mechanism" and "being"

Signed and Sealed this
First Day of October, 2019

Andrei Iancu
*Director of the United States Patent and Trademark Office*